United States Patent
Satoh et al.

(10) Patent No.: US 7,071,220 B2
(45) Date of Patent: Jul. 4, 2006

(54) N-SUBSTITUTED BENZOTHIOPHENESULFONAMIDE DERIVATIVES

(75) Inventors: Shoji Satoh, Saitama (JP); Akira Tatsui, Fukushima (JP); Takeshi Hasegawa, Fukushima (JP); Hideki Yamada, Saitama (JP); Shin-ichi Kazayama, Saitama (JP); Takahiro Morita, Saitama (JP); Hidekazu Masaki, Saitama (JP); Atsuo Takahashi, Saitama (JP); Fumiya Yoneyama, Fukushima (JP); Tetsuo Kuze, Fukushima (JP); Yusuke Mizuno, Saitama (JP); Mizuo Miyazaki, Kyoto (JP); Shinji Takai, Osaka (JP)

(73) Assignee: Toa Eiyo Ltd., Tokyo (JP)

( * ) Notice: Subject to any disclaimer, the term of this patent is extended or adjusted under 35 U.S.C. 154(b) by 263 days.

(21) Appl. No.: 10/388,378

(22) Filed: Mar. 13, 2003

(65) Prior Publication Data

US 2003/0229126 A1 Dec. 11, 2003

Related U.S. Application Data

(63) Continuation-in-part of application No. PCT/JP01/08061, filed on Sep. 17, 2001.

(30) Foreign Application Priority Data

| Sep. 18, 2000 | (JP) | ............................ P2000-282046 |
| Apr. 20, 2001 | (JP) | ............................ P2001-122972 |
| Mar. 15, 2002 | (JP) | ............................ P2002-072305 |
| Mar. 15, 2002 | (JP) | ............................ P2002-072306 |
| Mar. 15, 2002 | (JP) | ............................ P2002-072307 |

(51) Int. Cl.
| A61K 31/425 | (2006.01) |
| A61K 31/42  | (2006.01) |
| A61K 31/415 | (2006.01) |
| C07D 233/02 | (2006.01) |
| C07D 277/28 | (2006.01) |

(52) U.S. Cl. ...................... 514/365; 514/374; 514/397; 548/311.4; 548/205; 548/146
(58) Field of Classification Search ................ 514/365, 514/374, 397; 548/311.4, 205, 146
See application file for complete search history.

(56) References Cited

U.S. PATENT DOCUMENTS

| 5,514,691 | A  | * | 5/1996  | Chan et al. .................. 514/312 |
| 5,972,986 | A  | * | 10/1999 | Seibert et al. ............... 514/406 |
| 6,423,717 | B1 | * | 7/2002  | Bromidge et al. ...... 514/252.13 |
| 6,426,356 | B1 | * | 7/2002  | Baxter et al. ................ 514/365 |
| 6,433,005 | B1 | * | 8/2002  | McLaren et al. ........... 514/443 |
| 6,503,935 | B1 | * | 1/2003  | Altenbach et al. .......... 514/365 |
| 6,525,202 | B1 | * | 2/2003  | Hu et al. ..................... 546/223 |
| 6,552,031 | B1 | * | 4/2003  | Burch et al. ................. 514/282 |
| 6,579,895 | B1 | * | 6/2003  | Karim et al. ................ 514/406 |
| 6,583,157 | B1 | * | 6/2003  | McGee et al. ............... 514/312 |
| 6,613,789 | B1 | * | 9/2003  | Khanna et al. .............. 514/397 |
| 6,699,884 | B1 | * | 3/2004  | Brown et al. ............... 514/336 |
| 6,716,991 | B1 | * | 4/2004  | Talley et al. ............. 548/377.1 |

FOREIGN PATENT DOCUMENTS

| JP | 2000-95770-  | 4/2000  |
| JP | 2001-97946-  | 4/2001  |
| WO | WO 96/31492- | 10/1996 |
| WO | WO 97/11941- | 4/1997  |
| WO | WO 98/27081  | 6/1998  |
| WO | WO 99/37623  | 7/1999  |
| WO | WO 99/42465- | 8/1999  |
| WO | WO 00/10982  | 3/2000  |
| WO | WO 00/12073  | 3/2000  |
| WO | WO 00/12623- | 3/2000  |

OTHER PUBLICATIONS

XP002308847, Pailer et al., Chemical Abstracts (1962).
Supplementary European Search Report for EPO1967708 dated Dec. 3, 2004.

* cited by examiner

*Primary Examiner*—Deborah Lambkin
(74) *Attorney, Agent, or Firm*—Darby & Darby

(57) ABSTRACT

The present invention relates to an N-substituted benzothiophenesulfonamide derivative or a pharmaceutically acceptable salt thereof and applications thereof. Furthermore, it provides an agent for preventing or treating cardiac or circulatory disease and so on caused by abnormal increase of production of angiotensin II or endothelin I based on chymase activity, or by activation of mast cell, and an agent for preventing adhesion after surgery, wherein the agent has a selective inhibitory action on chymase.

14 Claims, No Drawings

N-SUBSTITUTED BENZOTHIOPHENESULFONAMIDE DERIVATIVES

This is a continuation-in-part of International Patent Application No. PCT/JP01/08061, filed Sep. 17, 2001, which claims priority of Japanese Patent Application No. 2000-282046, filed Sep. 18, 2000 and claims priority of Japanese Patent Application No. 2001-122972, filed Apr. 20, 2001. The International Application was published in Japanese on Mar. 21, 2002 as WO 02/22595 A1 under PCT Article 21 (2). This application also claims priority to Japanese Application No. 2002-072305, filed Mar. 15, 2002, Japanese Application No. 2002-072306, filed Mar. 15, 2002, and Japanese Application No. 2002-072307, filed Mar. 15, 2002.

FIELD OF THE INVENTION

The present invention relates to medicaments, especially N-substituted benzothiophenesulfonamide derivatives or salts thereof which selectively inhibit chymase, and chymase inhibitors containing the same as the active ingredient. Since the compounds have a selective inhibitory action on chymase, they are useful as agents for preventing or treating hypertension, hypercardia, cardiac infarction, arteriosclerosis, diabetic or non-diabetic renal diseases, diabetic retinopathy, restenosis after percutaneous transluminal coronary angioplasty (hereinafter, abbreviated as PTCA), intimal thickening after bypass grafting, chronic rheumatism, keloid, psoriasis, allergy, inflammation, asthma, atopic dermatitis, solid tumors and pulmonary hypertension caused by abnormal increase of production of angiotensin II (hereinafter, abbreviated as Ang II) or endothelin I (hereinafter, abbreviated as ET-1) based on chymase activity, or by activation of mast cell. In addition, the compounds of the invention are also useful as agents for preventing postoperative adhesion.

BACKGROUND OF THE INVENTION

Since Ang II and ET-1 have a cell growth-accelerating action in addition to a blood pressure-elevating action, they are considered as causative agents or risk factors for diseases such as hypertension, hypercardia, cardiac infarction, arteriosclerosis, diabetic or non-diabetic renal diseases and restenosis after PTCA. Moreover, it is known that Ang II is formed from angiotensin I (hereinafter, abbreviated as Ang I) by angiotensin converting enzyme (hereinafter, abbreviated as ACE), and a large number of ACE inhibitors have been developed as agents for preventing or treating the above diseases. On the other hand, it is known that ET-1 is a physiologically active peptide composed of 21 amino acid residues (hereinafter, abbreviated as ET(1-21)) which is formed from big endothelin (hereinafter, abbreviated as Big ET-1) by endothelin converting enzyme (hereinafter, abbreviated as ECE), but ECE inhibitors and ET-1 receptor antagonists are still in developmental stages as medicaments.

Recently, in addition to ACE, an enzyme producing Ang II from Ang I has been discovered and named chymase. Urata et al. purified chymase from human heart and has shown that 70 to 80% amount of Ang II produced in heart and blood vessels was due to chymase (J. Biol. Chem., 265, 22348 (1990). Moreover, when the fact that no effectiveness of ACE inhibitors on restenosis after PTCA is observed [MERCAPTOR study (Circulation, 86(1), 100 (1992)) and MARCAPTOR study (J. Am. Coll. Cardiol., 27(1), p. 1 (1996))] and the fact that chymase inhibitors are effective on a canine intimal thickening model of grafted blood vessel using jugular vein (Miyazaki, Takai et al.; Febs. Lett., 467, 141 (2000)) are together considered, it is important to inhibit chymase rather than ACE for preventing and treating cardiac and circulatory diseases and the like caused by abnormal increase of the production of Ang II, and thus the application of chymase inhibitors to cardiac and circulatory diseases is suggested.

Furthermore, in the recent past, it has been revealed that chymase specifically degrades Big ET-1 into a physiologically active peptide composed of 31 amino acid residues (hereinafter, abbreviated as ET(1-31)). It has been reported that the ET(1-31) acts on the receptor on which original ET(1-21) acts, to cause bronchoconstriction and vasoconstriction (Kido et al.; J. Immunol., 159, 1987 (1997)). In this connection, with regard to the concentration in human blood, both of ET(1-31) and ET(1-21) have about the same distribution and activity, and after cardiac infarction, ET(1-31) increases more largely than ET(1-21) does, which is maintained for two weeks after the incidence (Tamaki, Nishisu et al.; Jpn. J. Pharmacol., 82(suppl I), 26 (2000)), and the fact suggests importance of inhibition of chymase and application of chymase inhibitors to cardiac and circulatory diseases.

Accordingly, chymase is considered to participate in production and degradation of physiologically active peptides, remodeling of extracellular matrix, network with cytokine, immunity, and the like and contribute to restoration of metabolic turnover. Thus, a chymase inhibitor is expected to apply to cardiac and circulatory diseases.

Moreover, as a result of administration of Ang II into a sponge in a hamster subdermally sponge-implanted model, removal of the sponge after 7 days, and measurement of hemoglobin content, vascularization was observed (mainly capillary vessels). When ovalbumin (10 μg/site/day) as an antigen is administered to a sensitized animal via sponge, vascularization occurs as in the case of Compound 48/80. This vascularization was also inhibited by chymostatin (Muramatsu et al.; J. Biol. Chem., 275(8), 5545 (2000)). The above results indicate that activation of mast cells by antigen stimulation can also cause vascularization, and chymase may be involved in this process. Thus, new roles of chymase are suggested in a variety of inflammatory allergy diseases. From such a viewpoint, a chymase inhibitor is expected to exhibit effects on solid tumors, diabetic retinopathy, rheumatoid arthritis and atherosclerosis.

Currently, as inhibitors against chymase, peptide-type chymase inhibitors are disclosed in JP-A-10-7661, JP-A-11-49739, JP-A-11-246437, WO98/09949, WO98/18794, WO99/45928, WO99/32459 and WO00/06594. On the other hand, non-peptide-type chymase inhibitors are disclosed in JP-A-10-87493, JP-A-10-245384, JP-A-12-95770, WO96/04248, WO97/11941, WO99/09977, WO00/03997, WO00/05204, WO00/10982, WO00/32587, WO01/32214, WO01/32621 and WO01/83471. However, until now, no clinically applicable chymase inhibitor has been found. Accordingly, it is desired to develop a clinically applicable chymase inhibitor which enables prevention and treatment of cardiac and circulatory diseases and the like caused by abnormal increase of production of Ang II and ET-1, or by activation of mast cell.

Pulmonary hypertension as above is a pathological condition in which the average blood pressure of pulmonary artery is increased (25 mmHg or more) at rest through elevation of pulmonary vascular resistance and which may result in an after effect of hemodynamic change which is a possible danger to life. Slight physical exertion develops symptoms such as shortness of breath, breathing difficulty, fatigue, spasm of vertigo and loss of consciousness. In particular, pulmonary hypertension whose cause is unknown is called primary pulmonary hypertension, which breaks out with a frequency of 1 to 3 persons per 1 million persons and is a disease of a very bad prognosis, average survival time being 3 to 5 years from its diagnosis.

As a treatment for pulmonary hypertension, a therapy of constant intravenous infusion of a prostacyclin injection is introduced and shows a therapeutic effect (N. Engl. J. Med., 334, 296 (1996)). However, since a drug solution is constantly infused in this therapy, it is necessary to indwell a central venous catheter and carry a pump and hence the therapy imposes a heavy burden on patients and troubles such as infection at a catheter inserted part may sometimes occur. Moreover, a therapy of inhalation of nitrogen monoxide (NO) is effective for selective pulmonary vasodilation and is an indispensable therapy at the treatment of pulmonary hypertension in intensive care field, but the therapy requires a large-scale exclusive instrument as well as there are a lot of points to be improved in view of safety management (Nihon Rinsho, 59, 1126 (2001)).

In addition, application to pulmonary hypertension is investigated using a pharmaceutical agent such as an endothelin receptor blocker, a phosphodiesterase inhibitor, a thromboxane synthesis inhibitor or an angiotensin II receptor blocker. However, these agents are not used clinically because they exhibit insufficient effect or adverse effect, for example, most of them cause systemic blood pressure decrease (Nihon Rinsho, 59, 1139 (2001)).

There is a report that chymase-containing mast cells are accumulated in the lung tissue and pulmonary artery of pulmonary hypertension patients (Am. J. Respir. Crit. Care. Med., 160, 1303 (1999), Thorax., 54, 88 (1999)), and chymase released from the mast cells accumulated in the lung is considered to be one cause of thickening of vascular tunica media. Moreover, there is a suggestion that an acylsulfonamide derivative which is a chymase inhibitor may be an agent for treating or preventing pulmonary hypertension (JP-A-2001-97946). However, there is no report that a specific chymase inhibitor is actually effective for preventing or treating pulmonary hypertension.

Furthermore, a tissue adhesion in the body of mammals including human occurs after surgery in clinical fields such as gastroenterology, cardiology, orthopedics, gynecology and ophthalmology and exerts a strong influence on prognosis together with pain in patients. For example, in the case of abdominal operation, there arises a phenomenon that intraperitoneal organs such as abdominal wall and intestinal tracts mutually adhere after the operation, which sometimes causes ileus. In some cases, re-operation is required. In gynecological field, postoperative adhesion occurs in the patients who had an infection operation or intrapelvic operation, and sometimes causes sterility through tubal blockage. Also in cardiosurgery field, there is a case that re-operation is restricted by adhesion or there is a possible problem of bleeding at re-operation. In ophthalmic region, it becomes difficult to maintain quality of vision including insufficient control of intraocular pressure when organic adhesion or postoperative adhesion occurs.

As a prevention of postoperative adhesion, there are attempts to employ a variety of pharmaceutical agents or special films. As the pharmaceutical agents for preventing adhesion, there may be mentioned high-molecular weight polysaccharides having a wound surface-covering action such as sodium alginate, sodium chondroitin sulfate, high-molecular weight dextran and sodium hyaluronate. As agents for preventing postoperative adhesion of tubal orthosis, glucocorticoids such as dexamethasone and triamcinolone acetonide are employed. As films, films or sponges using gelatin (Gelfilm, Gelfoam (registered trademarks)), polytetrafluoroethylene sheets (Gore-Tex (registered trademark)) and hyaluronic acid sheets modified with carboxymethyl cellulose or the like (Seprafilm (registered trademark)) are employed. However, any agents are not satisfactory in view of the effects.

In this regard, recently, there are reported that a peptide Suc-Val-Pro-Phe$_{\psi}$(OPh)$_2$ which is a chymase inhibitor suppresses adhesion of organs after rubbing the uterus of a hamster adhesion model (Eur. J. Pharmacol., 435, 265 (2002)) and also adhesion at filtering blebs in a canine trabeculectomy model (Nihon Ganka gakkai Zasshi, Vol. 106, (extra number), 131 (2002)). In addition, it is suggested that a chymase inhibitor which is a quinazoline derivative can be utilized for preventing postoperative adhesion through alleviation of extracellular matrix dysbolism (WO01/62292).

DISCLOSURE OF THE INVENTION

As a result of the extensive studies for achieving the above objects, the present inventors have found that an N-substituted benzothiophenesulfonamide derivative or a pharmaceutically acceptable salt thereof has an excellent and selective human chymase inhibitory activity and is stable even in rat blood plasma. The N-substituted benzothiophenesulfonamide derivative represented by formula (I) or a pharmaceutically acceptable salt thereof according to the invention has a strong inhibitory activity against chymase and is a extremely useful compound for preventing or treating cardiac or circulatory diseases and the like caused by abnormal increase of production of Ang II or ET-1 based on chymase activity, or by activation of mast cell.

The N-substituted benzothiophenesulfonamide derivative represented by formula (I) or a pharmaceutically acceptable salt thereof according to the invention is useful as an agent for preventing or treating pulmonary hypertension and as an agent for preventing adhesion.

Also, it has been found that compounds represented by formulae

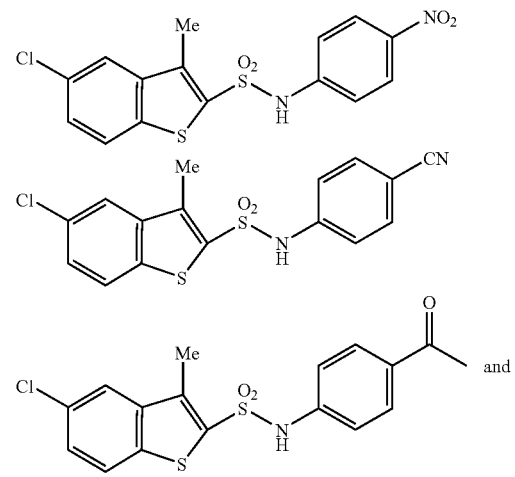

-continued

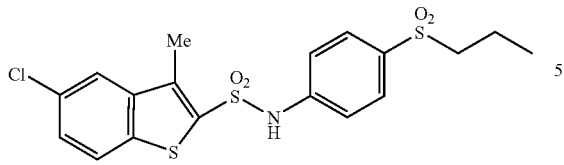

have a strong inhibitory activity against chymase and are extremely useful for preventing or treating cardiac or circulatory diseases and the like caused by abnormal increase of production of Ang II or ET-1, or by activation of mast cell based on chymase activity.

Namely, the invention relates to an N-substituted benzothiophenesulfonamide derivative represented by formula (I):

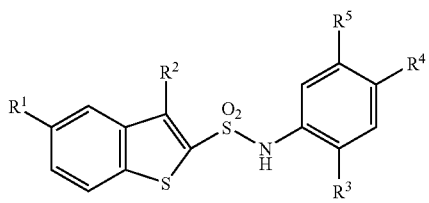

wherein $R^1$ represents a hydrogen atom, a halogen atom or a lower alkyl group;

$R_2$ represents a lower alkyl group;

$R^3$ and $R^4$ each may be the same or different and represents a hydrogen atom, a lower alkoxycarbonyl group, a lower alkylsulfonyl group, a benzoyl group, an acyl group having 1 to 4 carbon atoms, a lower alkoxy group, a lower alkoxycarbonylmethylthioacetyl group, a nitro group, —CONHR$^6$ in which R$^6$ represents a hydrogen atom, a lower alkoxycarbonylmethyl group, a carboxymethyl group or —CH(CH$_2$OH)COOR$^7$ in which R$^7$ represents a hydrogen atom or a lower alkyl group, a group represented by formula:

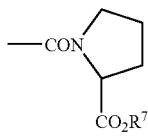

in which R$^7$ has the same meaning as above, a group represented by formula:

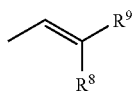

in which R$^8$ and R$^9$ each may be the same or different and represents a hydrogen atom, a lower alkyl group, a lower alkylsulfanyl group, a lower alkylsulfinyl group, a lower alkylsulfonyl group or a lower alkoxycarbonyl group, a hydroxy lower alkyl group, cyano group or a monocyclic heterocyclic group represented by formulae:

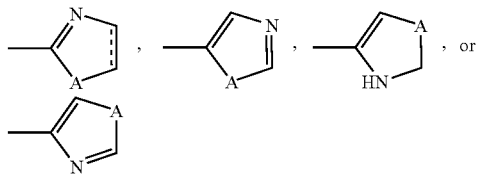

in which A represents an oxygen atom, a sulfur atom or NH and the dotted part represents a single bond or a double bond provided that the hydrogen atom on the ring may be replaced by a lower alkyl group which may be substituted by a halogen atom, a lower alkoxy group, a hydroxy lower alkyl group, a lower alkoxycarbonyl group or a carboxyl group, provided that R$^3$ and R$^4$ are not hydrogen atoms at the same time; and R$^5$ represents a hydrogen atom, a lower alkoxy group or a lower alkyl group, except the compounds represented by formulae

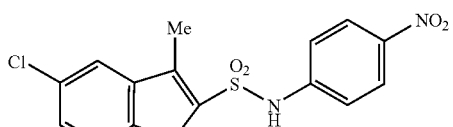

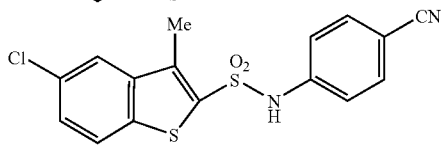

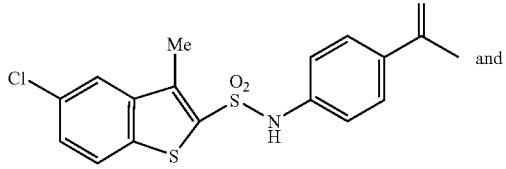

and

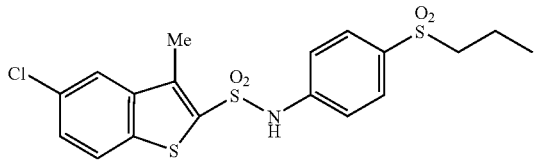

or a pharmaceutically acceptable salt thereof.

Moreover, the invention relates to the N-substituted benzothiophenesulfonamide derivative described above, wherein said derivative or a pharmaceutically acceptable salt thereof is selected from the group consisting of methyl 4-(5-chloro-3-methylbenzo[b]thiophene-2-sulfonylamino)-3-methanesulfonylbenzoate, sodium methyl 4-(5-chloro-3-methylbenzo[b]thiophene-2-sulfonylamino)-3-methanesulfonylbenzoate, isopropyl 4-(5-chloro-3-methylbenzo[b]thiophene-2-sulfonylamino)-3-methanesulfonylbenzoate, N-(4-acetyl-2-methanesulfonylphenyl)-5-chloro-3-methylbenzo[b]thiophene-2-sulfonamide, N-(4-benzoyl-2-methanesulfonylphenyl)-5-chloro-3-methylbenzo[b]thiophene-2-sulfonamide, methyl 4-(5-fluoro-3-methylbenzo[b]thiophene-2-sulfonylamino)-3-methanesulfonylbenzoate, methyl 4-(5-methyl-3-methylbenzo[b]thiophene-2-sulfonylamino)-3-methanesulfonylbenzoate, N-(4-acetyl-2-methanesulfonylphenyl)-5-chloro-3-methylbenzo[b]thiophene-2-sulfonamide, methyl 4-(3-methylbenzo[b]thiophene-2-sulfonylamino)-3-methanesulfonylbenzoate, 2-[4-(5-chloro-3-methylbenzo[b]thiophene-2-sulfonylamino)-3-methanesulfonylphenyl]oxazole-4-carboxylic acid, 2-[4-(5-fluoro-3-methylbenzo[b]thiophene-2-sulfonylamino)-3-methanesulfonylphenyl]oxazole-4-carboxylic acid, disodium 2-[4-(5-chloro-3-methylbenzo[b]thiophene-2-sulfonylamino)-3-methanesulfonylphenyl]oxazole-4-carboxylate, disodium 2-[4-(5-fluoro-3-methylbenzo[b]thiophene-2-sulfonylamino)-3-methanesulfonylphenyl]oxazole-4-carboxylate, 2-[4-(5-fluoro-3-methylbenzo[b]thiophene-2-sulfonylamino)-3-methanesulfonylphenyl]thiazole-4-carboxylic acid, 5-fluoro-N-[4-(4-hydroxymethylthiazol-2-yl)-2-methanesulfonylphenyl]-3-methylbenzo[b]thiophene-2-sulfonamide, 5-fluoro-N-[2-methanesulfonyl-4-(5-methoxy-4-methyloxazol-2-yl)phenyl]-3-methylbenzo[b]thiophene-2-sulfonamide, 5-fluoro-N-[2-methanesulfonyl-4-(5-methyloxazol-2-yl)phenyl]-3-methylbenzo[b]thiophene-2-sulfonamide and 5-fluoro-N-[2-methanesulfonyl-4-((E)-2-methanesulfinyl-2-methylsulfanylvinyl)phenyl]-3-methylbenzo[b]thiophene-2-sulfonamide.

Furthermore, the invention relates to a pharmaceutical composition comprising an N-substituted benzothiophenesulfonamide derivative represented by formula (I):

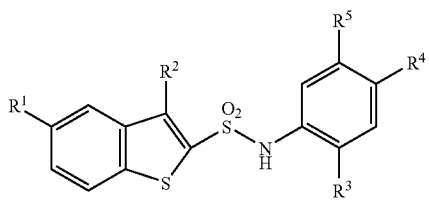

(I)

wherein $R^1$ represents a hydrogen atom, a halogen atom or a lower alkyl group;

$R^2$ represents a lower alkyl group;

$R^3$ and $R^4$ each may be the same or different and represents a hydrogen atom, a lower alkoxycarbonyl group, a lower alkylsulfonyl group, a benzoyl group, an acyl group having 1 to 4 carbon atoms, a lower alkoxy group, a lower alkoxycarbonylmethylthioacetyl group, a nitro group, —CONHR$^6$ in which $R^6$ represents a hydrogen atom, a lower alkoxycarbonylmethyl group, a carboxymethyl group or —CH(CH$_2$OH)COOR$^7$ in which $R^7$ represents a hydrogen atom or a lower alkyl group, a group represented by formula:

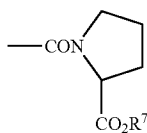

in which $R^7$ has the same meaning as above, a group represented by formula:

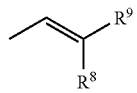

in which $R^8$ and $R^9$ each may be the same or different and represents a hydrogen atom, a lower alkyl group, a lower alkylsulfanyl group, a lower alkylsulfinyl group, a lower alkylsulfonyl group or a lower alkoxycarbonyl group, a hydroxy lower alkyl group, cyano group or a monocyclic heterocyclic group represented by formulae:

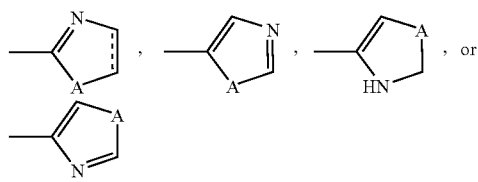

in which A represents an oxygen atom, a sulfur atom or NH and the dotted part represents a single bond or a double bond provided that the hydrogen atom on the ring may be replaced by a lower alkyl group which may be substituted by a halogen atom, a lower alkoxy group, a hydroxy lower alkyl group, a lower alkoxycarbonyl group or a carboxyl group, provided that $R^3$ and $R^4$ are not hydrogen atoms at the same time; and $R^5$ represents a hydrogen atom, a lower alkoxy group or a lower alkyl group, or a pharmaceutically acceptable salt thereof.

Still further, the invention relates to a chymase inhibitor comprising the N-substituted benzothiophenesulfonamide derivative or a salt thereof described above.

Moreover, the invention relates to an agent for preventing or treating hypertension, hypercardia, cardiac failure, cardiac infarction, arteriosclerosis, diabetic or non-diabetic renal disease, diabetic retinopathy, ischemic re-perfusion disorder, restenosis after PCTA, intimal thickening after bypass grafting, chronic rheumatism, keloid, psoriasis, allergy, inflammation, asthma, atopic dermatitis, solid tumors, pulmonary hypertension, wherein the agent comprises the N-substituted benzothiophenesulfonamide derivative or a pharmaceutically acceptable salt thereof described above.

Furthermore, the invention relates to an agent for preventing adhesion comprising the N-substituted benzothiophenesulfonamide derivative or a pharmaceutically acceptable salt thereof described above.

BEST MODE FOR CARRYING OUT THE INVENTION

Examples of the halogen atom for $R^1$ include a fluorine atom, a chlorine atom, a bromine atom or an iodine atom, and particularly, a fluorine atom or a chlorine atom is preferable.

Examples of the lower alkyl group for $R^1$, $R^2$, $R^5$, $R^7$, $R^8$ and $R^9$ include a methyl group, an ethyl group, a propyl group, an isopropyl group, a butyl group, an isobutyl group, a sec-butyl group or a tert-butyl group, and particularly, a methyl group or an ethyl group is preferable.

Examples of the lower alkoxycarbonyl group for $R^3$, $R^4$, $R^8$ and $R^9$ include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group or a tert-butoxycarbonyl group, and particularly, a methoxycarbonyl group, an ethoxycarbonyl group, an isopropoxycarbonyl group or a tert-butoxycarbonyl group is preferable.

Examples of the lower alkylsulfonyl group for $R^3$, $R^4$, $R^8$ and $R^9$ include a methanesulfonyl group, an ethanesulfonyl group, a propanesulfonyl group, an isopropanesulfonyl group, a butanesulfonyl group, an isobutanesulfonyl group, a sec-butanesulfonyl group or a tert-butanesulfonyl group, and particularly, a methanesulfonyl group or an ethanesulfonyl group is preferable.

Examples of the acyl group having 1 to 4 carbon atoms for $R^3$ and $R^4$ include a formyl group, an acetyl group, a propionyl group, a butyryl group or an isobutyryl group, and particularly, an acetyl group is preferable.

Examples of the lower alkoxy group for $R^3$, $R^4$ and $R^5$ include a methoxy group, an ethoxy group, a propoxy group, an isopropoxy group, a butoxy group, an isobutoxy group, a sec-butoxy group or a tert-butoxy group, and particularly, a methoxy group or an ethoxy group is preferable.

Examples of the lower alkoxycarbonylmethylthioacetyl group for $R^3$ and $R^4$ include a methoxycarbonylmethylthioacetyl group, an ethoxycarbonylmethylthioacetyl group, a propoxycarbonylmethylthioacetyl group, an isopropoxycarbonylmethylthioacetyl group, a butoxycarbonylmethylthioacetyl group, an isobutoxycarbonylmethylthioacetyl group, a sec-butoxycarbonylmethylthioacetyl group or a tert-butoxycarbonylmethylthioacetyl group, and particularly, a methoxycarbonylmethylthioacetyl group or an ethoxycarbonylmethylthioacetyl group is preferable.

In the case that $R^3$ and $R^4$ each is —CONHR$^6$, examples of the lower alkoxycarbonylmethyl group for $R^6$ include a methoxycarbonylmethyl group, an ethoxycarbonylmethyl group, a propoxycarbonylmethyl group, an isopropoxycarbonylmethyl group, a butoxycarbonylmethyl group, an isobutoxycarbonylmethyl group, a sec-butoxycarbonylmethyl group or a tert-butoxycarbonylmethyl group, and particularly, a methoxycarbonylmethyl group or an ethoxycarbonylmethyl group, or an isopropoxycarbonylmethyl group is preferable.

Examples of the hydroxy lower alkyl group for $R^3$ and $R^4$ include a linear or branched hydroxy lower alkyl group having 1 to 4 carbon atoms such as a hydroxymethyl group, a hydroxyethyl group, a hydroxypropyl group or a hydroxybutyl group, and particularly a hydroxymethyl group or a hydroxyethyl group is preferable.

Examples of the lower alkylsulfanyl group for $R^8$ and $R^9$ include a linear or branched lower alkylsulfanyl group having 1 to 4 carbon atoms such as a methylsulfanyl group, an ethylsulfanyl group, a propylsulfanyl group or a butylsulfanyl group, and particularly, a methylsulfanyl group or an ethylsulfanyl group.

Examples of the lower alkylsulfinyl group for $R^8$ and $R^9$ include a linear or branched lower alkylsulfinyl group having 1 to 4 carbon atoms such as a methanesulfinyl group, an ethanesulfinyl group, a propanesulfinyl group or a butanesulfinyl group, and particularly, a methanesulfinyl group or an ethanesulfinyl group is preferable.

As the group represented by the formula:

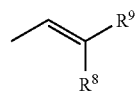

for example, a vinyl group, a methylsulfanylvinyl group, methanesulfinylvinyl group or 2-methanesulfinyl-2-methylsulfanylvinyl group is preferable.

The meanings of the lower alkoxy group, the hydroxy lower alkyl group and the lower alkoxycarbonyl group by which the hydrogen atom on the ring represented by the formulae:

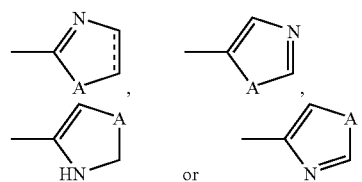

may be replaced are as mentioned in the above. Moreover, the lower alkyl group which may be substituted by a halogen atom means a lower alkyl group substituted by a fluorine atom, a chlorine atom, a bromine atom or an iodine atom in addition to the above-described lower alkyl group. Examples thereof include a chloromethyl group, a bromomethyl group, a dichloromethyl group or 1-chloroethyl group.

One or two of the lower alkyl groups which may be substituted by a halogen atom, lower alkoxy groups, hydroxy lower alkyl groups, lower alkoxycarbonyl groups or carboxyl groups may be present as substituent(s) on each heterocycle, and the substituents may be the same or different.

Examples of the monocyclic heterocylic group represented by the formulae:

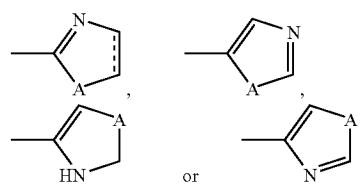

in which A represents an oxygen atom, a sulfur atom or NH and the dotted part represents a single bond or a double bond, include those represented by the following formulae.

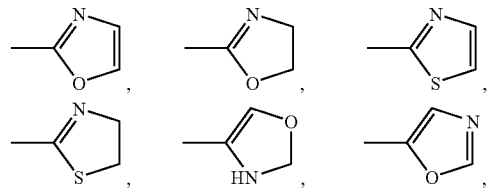

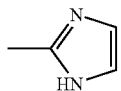

Specific examples of the monocyclic heterocylic group represented by the formulae:

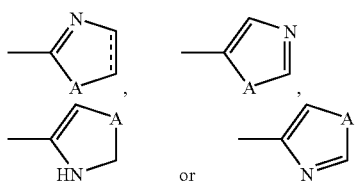

in which A represents an oxygen atom, a sulfur atom or NH and the dotted part represents a single bond or a double bond, as well as the hydrogen atom on the ring may be replaced by a lower alkyl group which may be substituted by a halogen atom, a lower alkoxy group, a hydroxy lower alkyl group, a lower alkoxycarbonyl group or a carboxyl group, preferably include those represented by the formulae:

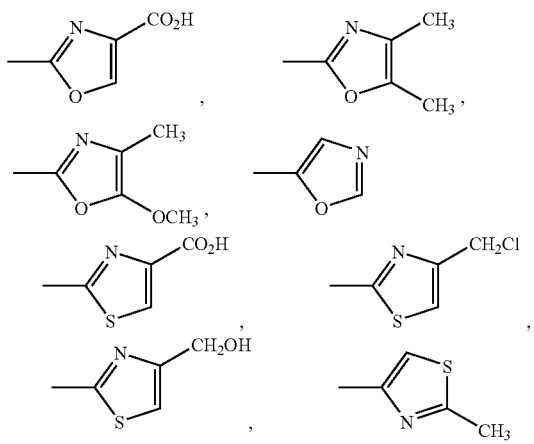

and these substituents are preferably substituted as $R^4$, In this case, it is further preferable that $R^3$ is a methanesulfonyl group and $R^5$ is a hydrogen atom.

In this regard, examples of specific compounds include methyl 4-(5-chloro-3-methylbenzo[b]thiophene-2-sulfonylamino)-3-methanesulfonylbenzoate, sodium methyl 4-(5-chloro-3-methylbenzo[b]thiophene-2-sulfonylamino)-3-methanesulfonylbenzoate, isopropyl 4-(5-chloro-3-methylbenzo[b]thiophene-2-sulfonylamino)-3-methanesulfonylbenzoate, N-(4-acetyl-2-methanesulfonylphenyl)-5-chloro-3-methylbenzo[b]thiophene-2-sulfonamide, N-(4-benzoyl-2-methanesulfonylphenyl)-5-chloro-3-methylbenzo[b]thiophene-2-sulfonamide, ethyl 4-(5-chloro-3-methylbenzo[b]thiophene-2-sulfonylamino)-3-methanesulfonylbenzoate, tert-butyl 4-(5-chloro-3-methylbenzo[b]thiophene-2-sulfonylamino)-3-methanesulfonylbenzoate, methyl 4-(5-chloro-3-methylbenzo[b]thiophene-2-sulfonylamino)-3-ethanesulfonylbenzoate, methyl 4-(5-chloro-3-methylbenzo[b]thiophene-2-sulfonylamino)-5-methanesulfonyl-2-methylbenzoate, dimethyl 4-(5-chloro-3-methylbenzo[b]thiophene-2-sulfonylamino)isophthalate, methyl 4-(5-chloro-3-methylbenzo[b]thiophene-2-sulfonylamino)-3-methoxybenzoate, methyl 4-(5-chloro-3-methylbenzo[b]thiophene-2-sulfonylamino)-3-nitrobenzoate, ethyl 4-(5-chloro-3-methylbenzo[b]thiophene-2-sulfonylamino)benzoate, 5-chloro-N-(2,4-dimethanesulfonylphenyl)-3-methylbenzo[b]thiophene-2-sulfonamide, N-(4-acetyl-2-nitrophenyl)-5-chloro-3-methylbenzo[b]thiophene-2-sulfonamide, 5-chloro-N-(4-hydroxymethyl-2-methanesulfonylphenyl)-3-methylbenzo[b]thiophene-2-sulfonamide, N-(4-benzoylphenyl)-5-chloro-3-methylbenzo[b]thiophene-2-sulfonamide, 5-chloro-N-(2-methanesulfonylphenyl)-3-methylbenzo[b]thiophene-2-sulfonamide, methyl 4-(5-fluoro-3-methylbenzo[b]thiophene-2-sulfonylamino)-3-methanesulfonylbenzoate, methyl 4-(5-methyl-3-methylbenzo[b]thiophene-2-sulfonylamino)-3-methanesulfonylbenzoate, N-(4-acetyl-2-methanesulfonylphenyl)-5-fluoro-3-methylbenzo[b]thiophene-2-sulfonamide, methyl 4-(3-methylbenzo[b]thiophene-2-sulfonylamino)-3-methanesulfonylbenzoate, methyl 2-[4-(5-chloro-3-methylbenzo[b]thiophene-2-sulfonylamino)-3-methanesulfonylphenyl]oxazole-4-carboxylate, methyl 2-[4-(5-fluoro-3-methylbenzo[b]thiophene-2-sulfonylamino)-3-methanesulfonylphenyl]oxazole-4-carboxylate, 2-[4-(5-chloro-3-methylbenzo[b]thiophene-2-sulfonylamino)-3-methanesulfonylphenyl]oxazole-4-carboxylic acid, 2-[4-(5-fluoro-3-methylbenzo[b]thiophene-2-sulfonylamino)-3-methanesulfonylphenyl]oxazole-4-carboxylic acid, disodium 2-[4-(5-chloro-3-methylbenzo[b]thiophene-2-sulfonylamino)-3-methanesulfonylphenyl]oxazole-4-carboxylate, disodium 2-[4-(5-fluoro-3-methylbenzo[b]thiophene-2-sulfonylamino)-3-methanesulfonylphenyl]oxazole-4-carboxylate, 5-fluoro-N-(2-methanesulfonyl-4-oxazol-5-ylphenyl)-3-methylbenzo[b]thiophene-2-sulfonamide, 2-[4-(5-fluoro-3-methylbenzo[b]thiophene-2-sulfonylamino)-3-methanesulfonylphenyl]thiazole-4-carboxylic acid, methyl 2-[4-(5-fluoro-3-methylbenzo[b]thiophene-2-sulfonylamino)-3-methanesulfonylphenyl]thiazole-4-carboxylate, 5-fluoro-N-[4-(4-hydroxymethylthiazol-2-yl)-2-methanesulfonylphenyl]-3-methylbenzo[b]thiophene-2-sulfonamide, N-[4-(4-chloromethylthiazol-2-yl)-2-methanesulfonylphenyl]-5-fluoro-3-methylbenzo[b]thiophene-2-sulfonamide, 5-fluoro-N-[2-methanesulfonyl-4-(4-methylthiazol-2-yl)phenyl]-3-methylbenzo[b]thiophene-2-sulfonamide, 5-fluoro-N-[2-methanesulfonyl-4-(2-methylthiazol-4-yl)phenyl]-3-methylbenzo[b]thiophene-2-sulfonamide, 5-fluoro-N-[2-methanesulfonyl-4-(5-methylthiazol-2-yl)phenyl]-3-methylbenzo[b]thiophene-2-sulfonamide, 5-fluoro-N-[2-methanesulfonyl-4-(5-methoxy-4-methylthiazol-2-yl)phenyl]-3-methylbenzo[b]thiophene-2-sulfonamide, 5-fluoro-N-[2-methanesulfonyl-4-(4,5-dimethylthiazol-2-yl)phenyl]-3-methylbenzo[b]thiophene-2-sulfonamide, 5-fluoro-N-[4-(4-hydroxymethyloxazol-2-yl)-2-methanesulfonylphenyl]-3-methylbenzo[b]thiophene-2-sulfonamide, N-[4-(4-chloromethyloxazol-2-yl)-2-methanesulfonylphenyl]-5-fluoro-3-methylbenzo[b]thiophene-2-sulfonamide, 5-fluoro-N-[2-methanesulfonyl-4-(4-methyloxazol-2-yl)phenyl]-3-methylbenzo[b]thiophene-2-sulfonamide, 5-fluoro-N-[2-methanesulfonyl-4-(5-methoxy-4-methyloxazol-2-yl)phenyl]-3-methylbenzo[b]thiophene-2-sulfonamide, 5-fluoro-N-[2-methanesulfonyl-4-(5-ethoxy-4-methyloxazol-2-yl)phenyl]-3-methylbenzo[b]thiophene-2-sulfonamide, 5-fluoro-N-[2-methanesulfonyl-4-(4,5-dimethyloxazol-2-yl)phenyl]-3- methylbenzo[b]thiophene-2-sulfonamide, 5-fluoro-N-[2-methanesulfonyl-4-(5-methyloxazol-2-yl)phenyl]-3-methylbenzo[b]thiophene-2-sulfonamide and 5-fluoro-N-[2-methanesulfonyl-4-((E)-2-methanesulfinyl-2-methylsulfanyl-vinyl)phenyl]-3-methylbenzo[b]thiophene-2-sulfonamide.

Of the above-described compounds, methyl 4-(5-chloro-3-methylbenzo[b]thiophene-2-sulfonylamino)-3-methanesulfonylbenzoate, sodium methyl 4-(5-chloro-3-methylbenzo[b]thiophene-2-sulfonylamino)-3-methanesulfonylbenzoate, isopropyl 4-(5-chloro-3-methylbenzo[b]thiophene-2-sulfonylamino)-3-methanesulfonylbenzoate, N-(4-acetyl-2-methanesulfonylphenyl)-5-chloro-3-methylbenzo[b]thiophene-2-sulfonamide, N-(4-benzoyl-2-methanesulfonylphenyl)-5-chloro-3-methylbenzo[b]thiophene-2-sulfonamide, methyl 4-(5-fluoro-3-methylbenzo[b]thiophene-2-sulfonylamino)-3-methanesulfonylbenzoate, methyl 4-(5-methyl-3-methylbenzo[b]thiophene-2-sulfonylamino)-3-methanesulfonylbenzoate, N-(4-acetyl-2-methanesulfonylphenyl)-5-fluoro-3-methylbenzo[b]thiophene-2-sulfonamide, methyl 4-(3-methylbenzo[b]thiophene-2-sulfonylamino)-3-methanesulfonylbenzoate, 2-[4-(5-chloro-3-methylbenzo[b]thiophene-2-sulfonylamino)-3-methanesulfonylphenyl]oxazole-4-carboxylic acid, 2-[4-(5-fluoro-3-methylbenzo[b]thiophene-2-sulfonylamino)-3-methanesulfonylphenyl]oxazole-4-carboxylic acid, disodium 2-[4-(5-chloro-3-methylbenzo[b]thiophene-2-sulfonylamino)-3-methanesulfonylphenyl]oxazole-4-carboxylate, disodium 2-[4-(5-fluoro-3-methylbenzo[b]thiophene-2-sulfonylamino)-3-methanesulfonylphenyl]oxazole-4-carboxylate, 2-[4-(5-fluoro-3-methylbenzo[b]thiophene-2-sulfonylamino)-3-methanesulfonylphenyl]thiazole-4-carboxylic acid, 5-fluoro-N-[4-(4-hydroxymethylthiazol-2-yl)-2-methanesulfonylphenyl]-3-methylbenzo[b]thiophene-2-sulfonamide, 5-fluoro-N-[2-methanesulfonyl-4-(5-methoxy-4-methyloxazol-2-yl)phenyl]-3-methylbenzo[b]thiophene-2-sulfonamide, 5-fluoro-N-[2-methanesulfonyl-4-(5-methyloxazol-2-yl)phenyl]-3-methylbenzo[b]thiophene-2-sulfonamide and 5-fluoro-N-[2-methanesulfonyl-4-((E)-2-methanesulfinyl-2-methylsulfanylvinyl)phenyl]-3-methylbenzo[b]thiophene-2-sulfonamide are preferable.

The following will describe the process for producing the N-substituted benzothiophenesulfonamide derivative or a salt thereof of the invention. The compound of the general formula (I) of the invention can be produced through the production process illustrated by the following reaction scheme.

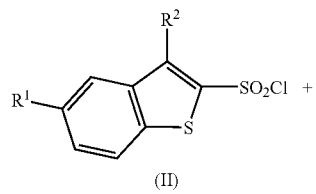

(II)

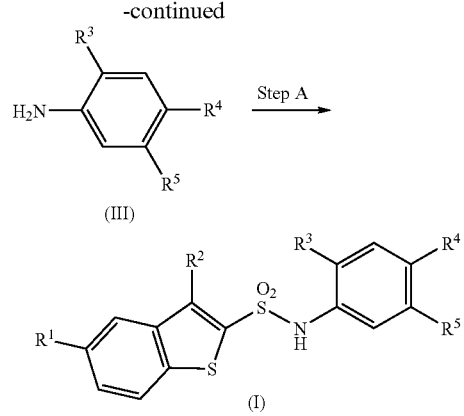

That is, the compound can be produced by reacting an amine represented by the compound (III) with an sulfonyl chloride (II) in the presence of a base such as sodium amide, lithium amide, sodium hydride, potassium carbonate, potassium tert-butoxide, triethylamine, ethyldiisopropylamine, pyridine, or 1,8-diazabicyclo[5.4.0]undec-7-ene (hereinafter, abbreviated as DBU) in a solvent such as dioxane, tetrahydrofuran (hereinafter, abbreviated as THF), acetone, dimethylformamide (hereinafter, abbreviated as DMF), dimethyl sulfoxide (hereinafter, abbreviated as DMSO), chloroform, pyridine or a mixed solvent thereof within the range of $-10°$ C. to a boiling point of the solvent.

In this connection, in the case of the compound of the general formula (I) wherein $R^3$ is a lower alkylsulfonyl group, $R^5$ is a hydrogen atom, and $R^4$ is a group represented by the general formula:

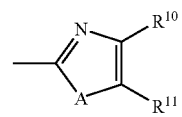

in which A has the same meaning as in the general formula (I) and $R^{10}$ and $R^{11}$ each may be the same or different and represents a hydrogen atom, a lower alkyl group which may be substituted by a halogen atom, a lower alkoxy group, a hydroxy lower alkyl group, a lower alkoxycarbonyl group or a carboxyl group, the compound can be also produced by the following production process.

In this case, the compound of the general formula (I) wherein $R^{11}$ is a substituent other than a hydrogen atom can be also produced through the production process illustrated by the following reaction scheme.

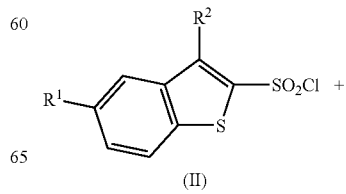

(II)

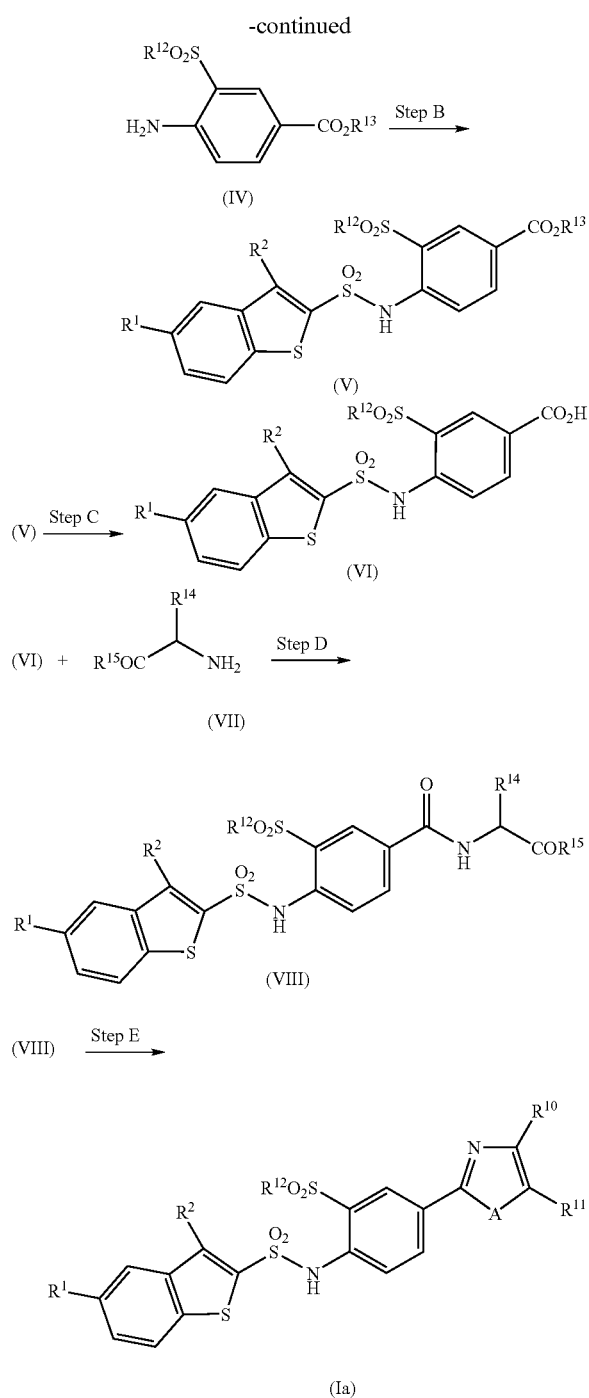

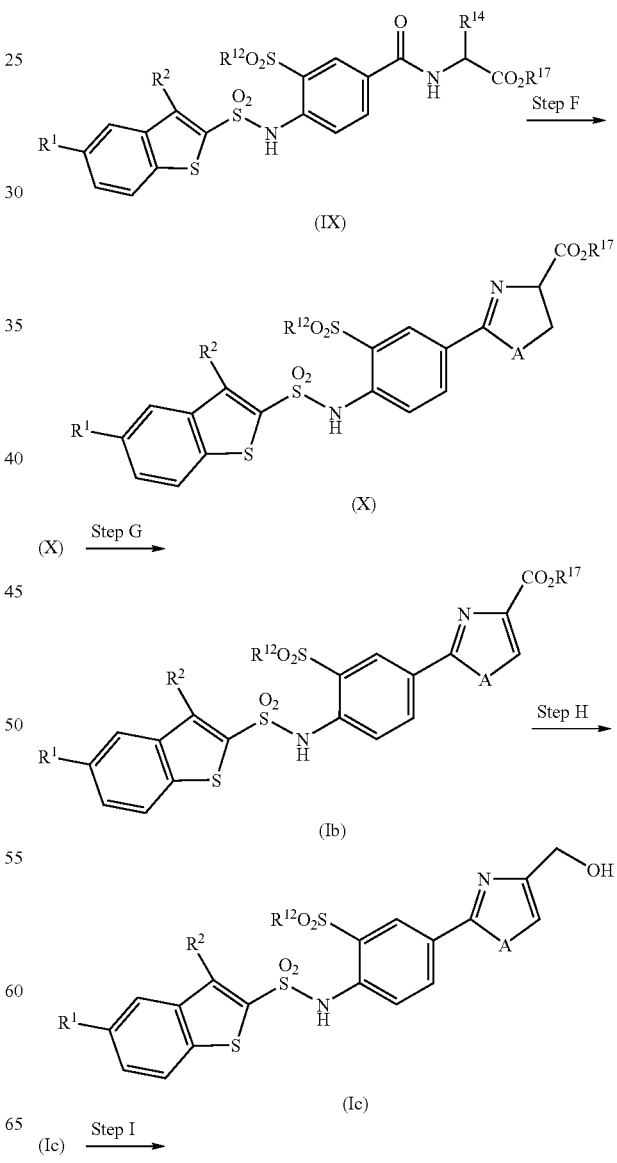

(Step B), and then ester hydrolysis was carried out to obtain a compound (VI) (Step C). Thereafter, the compound (VIII) wherein $R^{14}$ represents a hydrogen atom or a lower alkyl group and $R^{15}$ represents a lower alkyl group or a lower alkoxy group, is obtained by reacting the compound (VI) with an amine represented by the general formula (VII) in the presence of a base such as triethylamine, ethyldiisopropylamine or DBU using a condensing agent such as N,N'-dicyclohexylcarbodiimide (hereinafter, abbreviated as DCC) or 1-ethyl-3-(3-dimethylaminopropylcarbodiimide (hereinafter, abbreviated as EDC) (Step D), and then a compound (Ia) is obtained by using phosphorus oxychloride or diphosphorus pentasulfide (Step E), whereby the production is completed.

Furthermore, in the case of the compound wherein $R^{11}$ is a hydrogen atom, the compound of the general formula (I) can be also produced through the production process illustrated by the following reaction scheme.

That is, the compound (V) wherein $R^{12}$ and $R^{13}$ represents a lower alkyl group, is obtained by reacting an amine represented by the compound (IV) synthesized from 4-chlorobenzoic acid according to the method known in a literature (J. Med. Chem., 40, 2017 (1997)), with an sulfonyl chloride (II) in the presence of a base such as sodium amide, lithium amide, sodium hydride, potassium carbonate, potassium tert-butoxide, triethylamine, ethyldiisopropylamine, pyridine or DBU in a solvent such as dioxane, THF, acetone, DMF, DMSO, chloroform, pyridine or a mixed thereof within the range of −10° C. to a boiling point of the solvent -continued

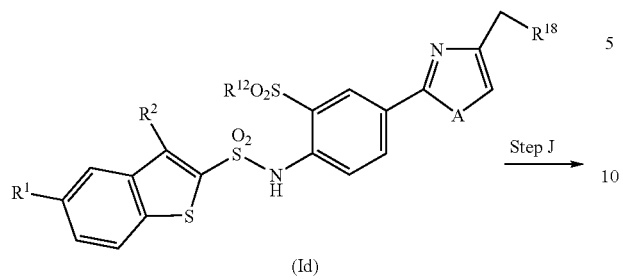
(Id)

Step J

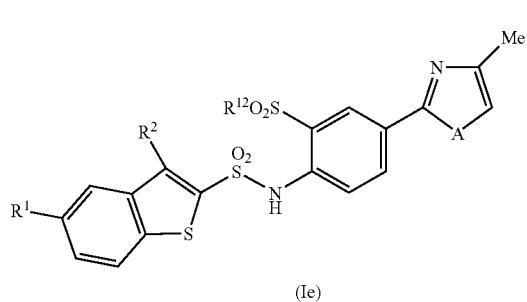
(Ie)

That is, a compound (Ib) is obtained in accordance with the method known in literatures (Tetrahedron Letters, 33, 907 (1992), J. Org. Chem., 38, 26 (1973), J. Org. Chem., 58, 4494 (1993), Org. Lett., 2, 1165 (2000), tetrahedron Letters, 42, 4171 (2001)) starting with a compound (IX) wherein $R^{16}$ represents a hydroxymethyl group or a mercaptomethyl group which may have a protective group such as a trityl group and $R^{17}$ represents a lower alkyl group (Steps and G). The compound (IX) is obtained by reacting the compound (VI) with serine ester hydrochloride, cysteine ester hydrochloride, S-tritylcysteine ester or the like in the presence of a base such as triethylamine, ethyldiisopropylamine or DBU using a condensing agent such as EDC. A compound (Ic) can be produced by further converting the ester group into a hydroxymethyl group through reduction (Step H). Also, a compound (Id) wherein $R^{18}$ represents a halogen atom can be produced by halogenating the compound (Ic) (Step I), and a compound (Ie) can be further produced by reducing the halogen atom of the compound (Id) to form a methyl group (Step J).

In this connection, a compound (If) can be produced by subjecting the compound (Ib) to ester hydrolysis (Step K).

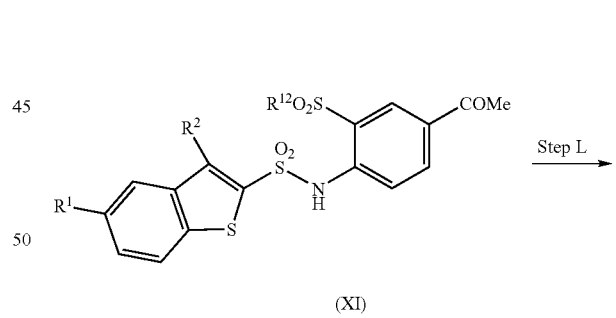
(Ib)

Step K

-continued

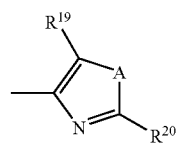
(If)

Also, in the case of the compound of the general formula (I) wherein $R^3$ is a lower alkylsulfonyl group, $R^5$ is a hydrogen atom, and $R^4$ is a group represented by the formula:

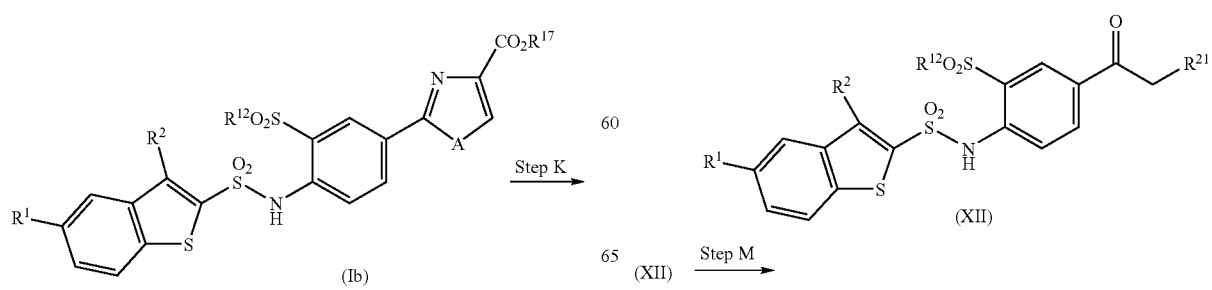

in which $R^{19}$ and $R^{20}$ each may be the same or different and represents a hydrogen atom, a lower alkyl group, which may be substituted by a halogen atom, a lower alkoxy group, a hydroxy lower alkyl group, a lower alkoxycarbonyl group or a carboxyl group, the compound of formula (I) can be also produced through the following production process illustrated by the following reaction scheme.

(XI)

Step L (XII)

Step M

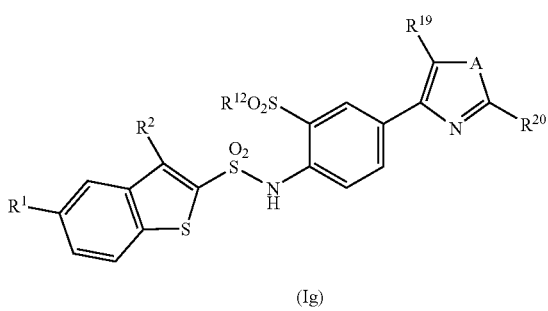

(Ig)

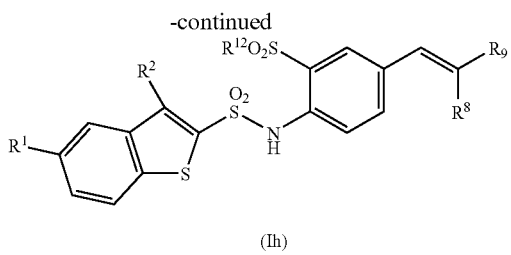

(Ih)

That is, a compound (XII) wherein $R^{21}$ represents a halogen atom is obtained from the compound (XI) wherein $R^{12}$ has the same meaning as above in accordance with the method known in a literature (JP-A-2000-256262) (Step L). Further, a compound (Ig) can be produced by subjecting the compound (XII) to ring closure with thioacetamide or formamide (Step M).

In this connection, in the case of the compound of formula (I) wherein $R^3$ is a lower alkylsulfonyl group, $R^5$ is a hydrogen atom, and $R^4$ is a group represented by the formula:

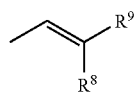

the compound can be also produced through the following production process illustrated by the following reaction scheme.

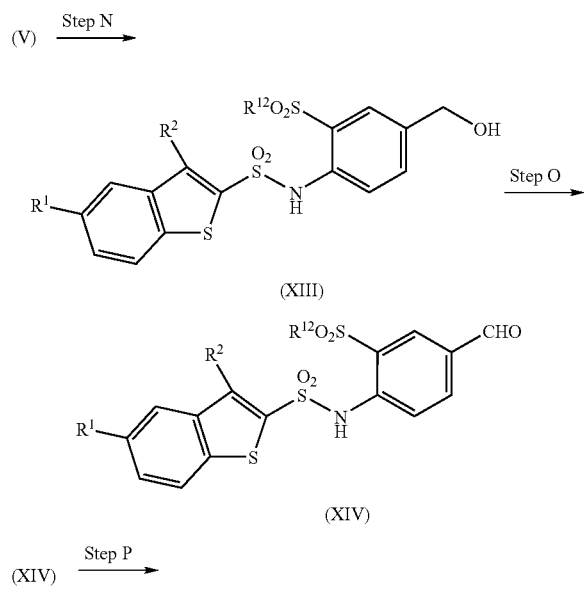

That is, a compound (XIV) is obtained by reducing the ester group of the compound (V) wherein $R^{12}$ has the same meaning as above, followed by oxidation to form an aldehyde group (Steps N and O) and then a compound (Ih) can be produced in accordance with the method known in a literature (Bull. Chem. Soc. Jpn., 52, 2013 (1979)) (Step P).

The thus formed compound of formula (I) can be isolated and purified by conventional methods such as recrystallization and column chromatography.

The compound of formula (I) of the invention can be formed into a pharmaceutically acceptable salt with an acid or base, e.g., a salt with an inorganic acid such as hydrochloride, hydrobromide, hydroiodide, sulfate, nitrate or phosphate; a salt with an organic acid such as acetate, trifluoroacetate, oxalate, fumarate, maleate, tartrate, mesylate or tosylate; a salt with an alkali metal such as sodium salt or potassium salt; or a salt with an alkaline earth metal such as calcium salt depending on the compound, by a usual method.

The compound of formula (I) sometimes includes optical isomers based on an asymmetric carbon atom. These various types of isomers isolated and mixtures of these isomers are also encompassed within the invention. Moreover, the compound of formula (I) of the invention includes hydrates and various solvates. All the crystal forms are also encompassed within the compound of formula (I).

The invention also includes a medicament containing the N-substituted benzothiophenesulfonamide derivative represented by the above formula (I) or a pharmaceutically acceptable salt thereof. The medicament includes an agent for inhibiting chymase activity.

The medicament is effective for diagnosing, preventing and/or treating diseases caused by abnormal increase of production of angiotensin II or endothelin I, or by activation of mast cell.

The above-described diseases include circulatory diseases and inflammatory allergosis, and the like.

Specifically, the diseases include hypertension, hypercardia, cardiac failure, cardiac infarction, arteriosclerosis, diabetic or non-diabetic renal disease, diabetic retinopathy, ischemic re-perfusion disorder, restenosis after PTCA, intimal thickening after bypass grafting, chronic rheumatism, keloid, psoriasis, allergy, inflammation, asthma, atopic dermatitis, solid tumors, pulmonary hypertension, and the like.

Moreover, the medicament is effective for preventing a tissue adhesion after surgery in clinical fields such as gastroenterology, cardiology, orthopedics, gynecology and ophthalmology.

The compound of formula (I) or a pharmaceutically acceptable salt thereof may be administered orally or parenterally. For the administration, pharmaceutically acceptable additives such as an excipient, a binder, a buffering agent, a thickener, a stabilizer, an emulsifier, a dispersing agent, a suspending agent, a preservative, and the like may be incorporated and preparations can be formulated in a usual manner.

Examples of preparations for oral administration include tablets including sugar-coated tablets and film-coated tablets, pills, granules, powders, capsules including soft capsules, liquids, syrups, emulsions, suspensions, and the like.

The preparations for oral administration can be manufactured with mixing additives usually employed in the pharmaceutical field in accordance with a known method. Examples of such additives include an excipient such as lactose, mannitol or anhydrous calcium hydrogen phosphate; a binder such as hydroxypropyl cellulose, methyl cellulose or polyvinylpyrrolidone; a disintegrator such as starch and carboxymethyl cellulose; a lubricant such as magnesium stearate or talc; and the like.

Parenteral administration may be conducted as injections, preparations for rectal administration, preparations for topical administration, and the like. The injections include aseptic solutions or suspensions. These injections can be manufactured by dissolving or suspending the compound of formula (I) or a pharmaceutically acceptable salt thereof in Japanese Pharmacopoeia-grade water for injection, for example. As needed, an isotonic agent such as sodium chloride, a buffering agent such as sodium dihydrogen phosphate or sodium monohydrogen phosphate, a solubilizing agent, or the like may be mixed. Moreover, the injections may be preparation to be dissolved before use (powder-packed or freeze-dried), which can be manufactured in a usual manner with adding an excipient such as mannitol or lactose.

Suppositories may be mentioned as the preparations for rectal administration. The suppositories are manufactured by dissolving or suspending the compound of formula (I) or a pharmaceutically acceptable salt thereof in a base material such as cacao butter or macrogol and molding the mixture in a mold. Moreover, the preparations for rectal administration may be manufactured by charging liquids or creams into containers for injection.

The preparations for topical application include liquids, eye-drops, creams, ointments, gel preparations, sprays, powders and the like. The liquids can be manufactured by adding the compound of formula (I) or a pharmaceutically acceptable salt thereof into water and further adding thereto a stabilizer, a solubilizer, a thickener, a dispersing agent, a suspending agent, and the like as needed. As the thickener, gelatin, sodium hyaluronate, high-molecular weight dextran, sodium alginate, sodium chondroitin sulfate or the like may be employed. The eye-drops can be manufactured by adding a buffering agent, a pH adjusting agent and an isotonic agent as well as a preservative. The creams and ointments can be manufactured using an aqueous or oily base material, e.g., water, liquid paraffin, a vegetable oil such as peanut oil or castor oil, or macrogol. The gel preparations can be manufactured by a known method using gelatin, pectin, carrageenan, agar, tragacanth, an arginate salt, a cellulose ether such as methyl cellulose or sodium carboxymethyl cellulose, a pectin derivative, a polyacrylate, a polymethacrylate, polyvinyl alcohol, polyvinyl pyrrolidone or the like. The sprays can be manufactured by dissolving or suspending the compound of formula (I) or a pharmaceutically acceptable salt thereof in water or the like and charging the mixture into spraying containers. In the case of the powders, the compound of formula (I) or a pharmaceutically acceptable salt thereof may be used as it is or may be mixed with an appropriate excipient to manufacture the powders.

Moreover, the compound of formula (I) or a pharmaceutically acceptable salt thereof can be administered after a gelatin sponge or a sheet of hyaluronic acid or the like is impregnated or coated with its solution.

Furthermore, the compound of formula (I) or a pharmaceutically acceptable salt thereof may be administered intranasally or by inhalation. Preparations for inhalation have an advantage of attaining quick action since the preparations deliver the compound directly to the pulmonary area. In the case of aerosols, particle size of the aerosols is preferably from 0.5 to 5 μm and the aerosols can be sprayed quantitatively using an appropriate propellant such as 1,1,1,2-tetrafluoroethane or 1,1,1,2,3,3,3-heptafluoropropane, carbon dioxide, air or another suitable gas. These preparations may be manufactured by a usual method, and a pH-adjusting agents such as citrate, lactate or phosphate buffer; a stabilizer e.g., an antioxidant such as sodium hydrogen sulfite or tocopherol or a metal chelating agent such as ethylenediamine tetraacetic acid; a preservative such as benzarconium chloride or a p-oxybenzoic acid ester; and the like may be added, if necessary.

The dose of the compound of formula (I) or pharmaceutically acceptable salt thereof per day for an adult is suitably from about 10 μg to 1 g, preferably about 100 μg to 100 mg in the case of oral administration. In the case of administering as injections, the dose may be from one tenth to a half of the dose in the case of oral administration. Moreover, in the case of directly administering to an operated part, the dose may be from 1 ng to 1 g. The dose can be appropriately changed depending on the conditions, body weight, age and the like of an individual patient.

The compound of formula (I) or a pharmaceutically acceptable salt thereof exhibits a low toxicity and no remarkable toxicity is observed through three days of observation after oral administration (single dose, 300 mg/kg) to 6-week-old male rats. Accordingly, these compounds are judged to be highly safe.

EXAMPLES

The following will describe the invention in more detail with reference to Examples and Test Examples, but the invention is not limited thereto.

Reference Example 1

[4-(5-Fluoro-3-methylbenzo[b]thiophene-2-sulfonylamino)-3-methanesulfonyl]benzoic Acid Into 500 mL of methanol was dissolved 24.8 g of methyl 4-(5-fluoro-3-methylbenzo[b]thiophene-2-sulfonylamino)-3-methanesulfonylbenzoate, and 50 mL of 1 mol/L sodium hydroxide was added thereto. After 3 hours of stirring under heating and refluxing, the solvent was removed by evaporation under reduced pressure and water was added to the resulting residue. The mixture was washed with ether. To the aqueous layer was added 2 mol/L hydrochloric acid, followed by extraction with ethyl acetate. The organic layer was washed with saturated brine and then dried over anhydrous sodium sulfate. The solvent was removed by evaporation under reduced pressure and the resulting residue was washed with ether to obtain 14.3 g of the title compound as colorless powder.

Melting point: 290° C.

$^1$H-NMR (CDCl$_3$): δ 2.66 (3H, s), 3.05 (3H, s), 6.76 (1H, dd, J=2.0, 8.6 Hz), 7.45 (1H, dd, J=2.0, 8.6 Hz), 7.75 (1H, dd, J=4.6, 9.0 Hz), 7.82 (1H, d, J=8.8 Hz), 8.17 (1H, dd, J=2.0, 8.8 Hz), 8.49 (1H, d, J=2.0 Hz).

IR ν$_{max}$ (KBr): 3239, 2925, 1687, 1609, 1501, 1442, 1421, 1400, 1356, 1287, 1161 cm$^{-1}$.

Reference Example 2

Methyl (2S)-2-[4-(5-fluoro-3-methylbenzo[b]thiophene-2-sulfonylamino)-3-methanesulfonylphenylcarboxyamido]propionate Into 100 mL of dichloromethane was suspended 3.78 g of L-alanine methyl ester hydrochloride, and 3.8 mL of triethylamine was added at 0° C. Thereto was added 100 mL of dichloromethane suspension of 10.0 g of [4-(5-fluoro-3-methylbenzo[b]thiophene-2-sulfonylamino)-3-methanesulfonyl]benzoic acid. After 5 minutes of stirring at the same temperature, 5.19 g of EDC hydrochloride was added and the mixture was stirred at room temperature for 19 hours. After the reaction was terminated with 1 mol/L hydrochloric acid, the dichloromethane layer was separated. After removal of the solvent by evaporation under reduced pressure, a mixed solution of ethyl acetate-THF (1/1) was added to the resulting residue, followed by successive washing with water and saturated brine and drying over anhydrous magnesium sulfate. The solvent was removed by evaporation under reduced pressure and the resulting residue was washed with methanol to obtain 9.22 g of the title compound as colorless powder.

Melting point: 162–163° C.

$^1$H-NMR (CDCl$_3$): δ 1.49 (3H, d, J=7.3 Hz), 2.69 (3H, s), 3.07 (3H, s), 3.79 (3H, s), 4.74 (1H, dq, J=7.3, 7.3 Hz), 6.96 (1H, d, J=7.3 Hz), 7.28 (1H, ddd, J=2.4, 8.6, 8.8 Hz), 7.47 (1H, dd, J=2.4, 9.2 Hz), 7.77 (1H, dd, J=4.7, 8.8 Hz), 7.81 (1H, d, J=8.7 Hz), 7.89 (1H, dd, J=2.0, 8.7 Hz), 8.25 (1H, d, J=2.0 Hz), 9.71 (1H, s).

IR ν$_{max}$ (KBr): 3323, 3222, 3068, 3003, 2924, 1737, 1636, 1607, 1496, 1306, 1165, 924 cm$^{-1}$.

Reference Example 3

4-(5-Fluoro-3-methylbenzo[b]thiophene-2-sulfonylamino)-3-methanesulfonyl]benzaldehyde Into 25 mL of ethyl acetate was dissolved 830 mg of 5-fluoro-N-(4-hydroxymethyl-2-methanesulfonylphenyl)-3-methylbenzo[b]thiophene-2-sulfonamide, and 4.15 g of active manganese dioxide was added thereto, followed by 5 hours of stirring at room temperature. The reaction solution was diluted with ethyl acetate and then was filtered through celite to remove manganese dioxide. The solvent was removed by evaporation under reduced pressure to obtain 696 mg of the title compound as colorless powder.

Melting point: 167–170° C.

$^1$H-NMR (CDCl$_3$): δ 2.70 (3H, s), 3.10 (3H, s), 7.31 (1H, ddd, J=2.4, 8.7, 9.0 Hz), 7.48 (1H, dd, J=2.4, 9.0 Hz), 7.78 (1H, dd J=4.5, 9.0 Hz), 7.96 (1H, d, J=8.7 Hz), 8.06 (1H, dd, J=2.1, 8.7 Hz), 8.36 (1H, d, J=2.1 Hz), 9.90 (1H, s), 9.92 (1H, s).

IR ν$_{max}$ (KBr): 3260, 1694, 1602, 1496, 1308, 1164, 912 cm$^{-1}$.

Example 1

Synthesis of Methyl 4-(5-chloro-3-methylbenzo[b]thiophene-2-sulfonylamino)-3-methanesulfonylbenzoate (Compound 1)

Into a mixed solvent of 20 mL of THF and 3 mL of DMF was dissolved 985 mg of methyl 4-amino-3-methanesulfonylbenzoate, followed by addition of 170 mg of sodium hydride (oily, 60%) at 0° C. After 20 minutes of stirring at the same temperature, 1.28 g of 5-chloro-2-chlorosulfonyl-3-methylbenzo[b]thiophene was added at 0° C., followed by 1 hour of stirring at room temperature. Further, 150 mg of sodium hydride (oily, 60%) was added at room temperature and the mixture was stirred for 2 hours at the same temperature. After confirmation of disappearance of the starting material, the reaction was terminated by adding saturated aqueous ammonium chloride solution at 0° C., followed by extraction with ethyl acetate. The organic layer was washed with saturated brine and then dried over anhydrous sodium sulfate. The solvent was removed by evaporation and the residue was purified by silica gel column chromatography (ethyl acetate/hexane=3/1) to obtain 911 mg of the title compound as colorless powder.

Melting point: 179–181° C.

$^1$H-NMR (CDCl$_3$): δ 2.70 (3H, s), 3.06 (3H, s), 3.90 (3H, s), 7.48 (1H, dd, J=2.1, 8.6 Hz), 7.74 (1H, d, J=8.6 Hz), 7.89 (1H, d, J=2.1 Hz), 7.86 (1H, d, J=8.8 Hz), 8.19 (1H, dd, J=2.0, 8.8 Hz), 8.50 (1H, d, J=2.0 Hz ), 9.84 (1H, s).

IR ν$_{max}$ (KBr): 3217, 1720, 1608, 1504, 1442, 1392, 1308, 1165, 1119 c m$^{-1}$.

Example 2

Synthesis of Ethyl 4-(5-chloro-3-methylbenzo[b]thiophene-2-sulfonylamino)-3-methanesulfonylbenzoate (Compound 2)

In the same manner as in Example 1, 529 mg of the title compound was obtained as colorless powder from 559 mg of ethyl 4-amino-3-methanesulfonylbenzoate.

Melting point: 167–169° C.

$^1$H-NMR (CDCl$_3$): δ 1.36 (3H, t, J=7.1 Hz), 2.70 (3H, s), 3.06 (3H, s), 4.36 (2H, q, J=7.1 Hz), 7.47 (1H, dd, J=2.0, 8.8 Hz), 7.74 (1H, d, J=8.8 Hz), 7.78 (1H, d, J=2.0 Hz), 7.86 (1H, d, J=8.8 Hz), 8.19 (1H, dd, J=2.0, 8.8 Hz), 8.50 (1H, d, J=2.0 Hz), 9.83 (1H, brs).

IR ν$_{max}$ (KBr): 3224, 2985, 1716, 1608, 1500, 1358, 1300, 1142 cm$^{-1}$.

Example 3

Synthesis of tert-butyl 4-(5-chloro-3-methylbenzo[b]thiophene-2-sulfonylamino)-3-methanesulfonylbenzoate (Compound 3)

In the same manner as in Example 1, 148 mg of the title compound was obtained as colorless powder from 128 mg of tert-butyl 4-amino-3-methanesulfonylbenzoate.

Melting point: 236–238° C.

$^1$H-NMR (CDCl$_3$): δ 1.54 (9H, s), 2.52 (3H, s), 3.28 (3H, s), 7.55–7.80 (4H, m), 8.00 (1H, s), 8.25–8.30 (1H, m).

IR ν$_{max}$ (KBr): 3467, 2974, 2327, 1705, 1662, 1597, 1477, 1396, 1296, 1130, 1099 cm$^{-1}$.

Example 4

Synthesis of Methyl 4-(5-chloro-3-methylbenzo[b]thiophene-2-sulfonylamino)-3-ethanesulfonylbenzoate (Compound 4)

In the same manner as in Example 1, 80 mg of the title compound was obtained as colorless powder from 76 mg of methyl 4-amino-3-ethanesulfonylbenzoate.

Melting point: 172–173° C.

$^1$H-NMR (CDCl$_3$): δ 1.27 (3H, t, J=7.3 Hz), 2.74 (3H, s), 3.24 (2H, q, J=7.3 Hz), 3.77 (3H, s), 7.20–7.31 (2H, m), 7.43–7.56 (3H, m), 8.31 (1H, s).

IR ν$_{max}$ (KBr): 3482, 3217, 2931, 1709, 1597, 1481, 1439, 1284, 1126 c m$^{-1}$.

Example 5

Synthesis of Methyl 4-(5-chloro-3-methylbenzo[b]thiophene-2-sulfonylamino)-5-methanesulfonyl-2-methylbenzoate (Compound 5)

Into 10 mL of THF was dissolved 135 mg of methyl 4-amino-5-methanesulfonyl-2-methylbenzoate, followed by addition of 22 mg of sodium hydride (oily, 60%) at room temperature. After 20 minutes of stirring at the same temperature, 130 mg of 5-chloro-2-chlorosulfonyl-3-methylbenzo[b]thiophene was added at 0° C., followed by 1 hour of stirring at room temperature and 5 hours of heating under refluxing. Further, 1 mL of DMF, 22 mg of sodium hydride (oily, 60%) and 50 mg of 5-chloro-2-chlorosulfonyl-3-methylbenzo[b]thiophene were added and the mixture was heated under refluxing for 2.5 hours. After confirmation of disappearance of the starting material, the reaction was terminated by adding saturated aqueous ammonium chloride solution at 0° C., followed by extraction with ethyl acetate. The organic layer was washed with saturated brine and then dried over anhydrous sodium sulfate. The solvent was removed by evaporation and the residue was purified by silica gel column chromatography (ethyl acetate/hexane=3/2) to obtain 102 mg of the title compound as colorless powder.

Melting point: 205–207° C.

$^1$H-NMR (CDCl$_3$): δ 2.65 (3H, s), 2.71 (3H, s), 3.04 (3H, s), 3.87 (3H, s), 7.49 (1H, dd, J=2.0, 8.6 Hz), 7.68 (1H, s), 7.77 (1H, d, J=8.6 Hz), 7.80 (1H, d, J=2.0 Hz), 8.42 (1H, s), 9.73 (1H, s).

IR ν$_{max}$ (KBr): 3259, 1728, 1604, 1554, 1504, 1439, 1385, 1354, 1300, 1257, 1157, 1092 cm$^{-1}$.

Example 6

Synthesis of Dimethyl 4-(5-chloro-3-methylbenzo[b]thiophene-2-sulfonylamino)isophthalate (Compound 6)

Into 8 mL of THF was dissolved 115 mg of dimethyl 4-aminoisophthalate, followed by addition of 22 mg of sodium hydride (oily, 60%). After 20 minutes of stirring at room temperature, 130 mg of 5-chloro-2-chlorosulfonyl-3-methylbenzo[b]thiophene was added at the same temperature, followed by 30 minutes of stirring at room temperature. Further, 26 mg of sodium hydride (oily, 60%) was added and the whole was heated under refluxing for 6 hours. After confirmation of disappearance of the starting material, the reaction was terminated by adding saturated aqueous ammonium chloride solution at 0° C., followed by extraction with ethyl acetate. The organic layer was washed with saturated brine and then dried over anhydrous sodium sulfate. The solvent was removed by evaporation and the residue was purified by silica gel column chromatography (ethyl acetate/hexane 1/1) to obtain 62 mg of the title compound as light yellow amorphous.

$^1$H-NMR (CDCl$_3$): δ 2.64 (3H, s), 3.88 (3H, s), 3.95 (3H, s), 7.44 (1H, dd, J=2.0, 8.8 Hz), 7.71 (1H, d, J=8.8 Hz), 7.74 (1H, d, J=2.0 Hz), 7.86 (1H, d, J=8.8 Hz), 8.11 (1H, dd, J=2.0, 8.8 Hz), 8.63 (1H, d, J=2.0 Hz).

IR ν$_{max}$ (KBr): 3440, 3140, 2954, 1724, 1693, 1608, 1500, 1439, 1331, 1246, 1165, 1119 cm$^{-1}$.

Example 7

Synthesis of Methyl 4-(5-chloro-3-methylbenzo[b]thiophene-2-sulfonylamino)-3-methoxybenzoate (Compound 7)

Into 4 mL of pyridine were dissolved 120 mg of methyl 4-amino-3-methoxybenzoate and 150 mg of 5-chloro-2-chlorosulfonyl-3-methylbenzo[b]thiophene, followed by 14 hours of stirring at room temperature. After confirmation of disappearance of the starting material, the reaction was terminated by adding water at 0° C., followed by extraction with ethyl acetate. The organic layer was washed with saturated brine and then dried over anhydrous sodium sulfate. The solvent was removed by evaporation and then the residue was purified by silica gel column chromatography (chloroform/methanol=9/1) to obtain 110 mg of the title compound as colorless amorphous.

$^1$H-NMR (CDCl$_3$): δ 2.55 (3H, s), 3.79 (3H, s), 3.86 (3H, s), 7.42 (1H, dd, J=2.0, 8.6 Hz), 7.45 (1H, dd, J=2.0, 8.6 Hz), 7.61 (1H, d, J=2.0Hz), 7.62 (1H, d, J=8.6 Hz), 7.68 (1H, d, J=8.6 Hz), 7.71 (1H, d, J=2.0Hz).

IR ν$_{max}$ (KBr): 3248, 2951, 1716, 1601, 1512, 1439, 1350, 1284, 1242, 1161, 1115 cm$^{-1}$.

Example 8

Synthesis of Methyl 4-(5-chloro-3-methylbenzo[b]thiophene-2-sulfonylamino)-3-nitrobenzoate (Compound 8)

In the same manner as in Example 6, 146 mg of the title compound was obtained as yellow powder from 122 mg of methyl 4-amino-3-nitrobenzoate.

Melting point: 164–165° C.

$^1$H-NMR (CDCl$_3$): δ 2.47 (3H, s), 3.84 (3H, s), 7.56 (1H, d, J=8.6 Hz), 7.57 (1H, brd, J=8.6 Hz), 8.01 (1H, d, J=1.8 Hz), 8.06 (1H, d, J=8.6 Hz), 8.07 (1H, brd, J=8.6 Hz), 8.25 (1H, d, J=1.8 Hz).

IR ν$_{max}$ (KBr): 3442, 3237, 3060, 2949, 1732, 1621, 1535, 1507, 1440, 1356, 1297, 1164, 1106 cm$^{-1}$.

Example 9

Synthesis of 5-chloro-N-(2,4-dimethanesulfonylphenyl)-3-methylbenzo[b]thiophene-2-sulfonamide (Compound 9)

In the same manner as in Example 6, 368 mg of the title compound was obtained as colorless powder from 200 mg of 2,4-dimethanesulfonylaniline.

Melting point: 176–178° C.

$^1$H-NMR (DMSO-d$_6$): δ 2.65 (3H, s), 3.00 (3H, s), 3.07 (3H, s), 7.44 (1H, dd, J=1.8, 8.6 Hz), 7.71 (1H, d, J=8.6 Hz), 7.76 (1H, d, J=1.8 Hz), 7.92 (1H, d, J=8.8 Hz), 8.04 (1H, dd, J=1.8, 8.8 Hz), 8.34 (1H, d, J=1.8 Hz).

IR $\nu_{max}$ (KBr): 3236, 3020, 1593, 1489, 1392, 1354, 1304, 1157 cm$^{-1}$.

Example 10

Synthesis of N-(4-acetyl-2-nitrophenyl)-5-chloro-3-methylbenzo[b]thiophene-2-sulfonamide (Compound 10)

In the same manner as in Example 6, 59 mg of the title compound was obtained as colorless powder from 96 mg of 4-acetyl-2-nitroaniline.

Melting point: 130–131° C.

$^1$H-NMR (CDCl$_3$): δ 2.58 (3H, s), 2.69 (3H, s), 7.46 (1H, dd, J=2.0, 8.6 Hz), 7.73 (1H, d, J=8.6 Hz), 7.78 (1H, d, J=2.0 Hz), 8.05 (1H, d, J=8.8 Hz), 8.16 (1H, dd, J=1.8, 8.8 Hz), 8.74 (1H, d, J=1.8 Hz).

IR $\nu_{max}$ (KBr): 3745, 3479, 3363, 3262, 3089, 2927, 2858, 1689, 1620, 1531, 1419, 1354, 1115, 1080 cm$^1$.

Example 11

Synthesis of N-(4-acetyl-2-methanesulfonylphenyl)-5-chloro-3-methylbenzo[b]thiophene-2-sulfonamide (Compound 11)

Into a mixed solvent of 20 mL of THF and 5 ml of DMF was dissolved 241 mg of 4-amino-3-methanesulfonylacetophenone, followed by addition of 136 mg of sodium hydride (oily, 60%) at –78° C. After 20 minutes of stirring at the same temperature, 350 mg of 5-chloro-2-chlorosulfonyl-3-methylbenzo[b]thiophene was added at –78° C., and the mixture was gradually warmed and stirred at –10° C. for 1 hour. After confirmation of disappearance of the starting material, the reaction was terminated by adding saturated aqueous ammonium chloride solution at 0° C., followed by extraction with ethyl acetate. The organic layer was washed with saturated brine and then dried over anhydrous sodium sulfate. The solvent was removed by evaporation and the residue was purified by silica gel column chromatography (ethyl acetate/hexane=1/1) to obtain 427 mg of the title compound as colorless powder.

Melting point: 207–209° C.

$^1$H-NMR (CDCl$_3$): δ 2.56 (3H, s), 2.69 (3H, s), 3.07 (3H, s), 7.46 (1H, dd, J=1.9, 8.7 Hz), 7.72–7.79 (2H, m), 7.86 (1H, d, J=8.6 Hz), 8.10 (1H, d, J=8.6 Hz), 8.40 (1H, d, J=1.9 Hz).

IR $\nu_{max}$ (KBr): 3456, 3236, 3086, 3005, 2924, 2854, 1670, 1593, 1489, 1389, 1354, 1308, 1261, 1165, 1130, 1053 cm$^{-1}$.

Example 12

Synthesis of N-(4-benzoyl-2-methanesulfonylphenyl)-5-chloro-3-methylbenzo[b]thiophene-2-sulfonamide (Compound 12)

In the same manner as in Example 11, 68 mg of the title compound was obtained as colorless powder from 94 mg of 4-amino-3-methanesulfonylbenzophenone.

Melting point: 144–146° C.

$^1$H-NMR (CDCl$_3$): δ 2.70 (3H, s), 3.08 (3H, s), 7.45–7.50 (3H, m), 7.58–7.62 (2H, m), 7.68–7.71 (4H, m), 7.85 (1H, d, J=8.6 Hz) 7.97 (1H, d, J=8.6 Hz), 8.31 (1H, brs).

IR $\nu_{max}$ (KBr): 3456, 3248, 3001, 2927, 2858, 2256, 1709, 1655, 1597, 1496, 1450, 1389, 1350, 1308, 1161, 1130, 1084 cm$^{-1}$.

Example 13

Synthesis of 5-chloro-N-(4-hydroxymethyl-2-methanesulfonylphenyl)-3-methylbenzo[b]thiophene-2-sulfonamide (Compound 13)

Into 10 mL of toluene was dissolved 305 mg of Compound 1, and the solution was cooled to –78° C., followed by addition of 2.2 mL of 1.01 mol/L toluene solution of diisobutylaluminum hydride. After 20 minutes of stirring at the same temperature, the mixture was gradually warmed to 0° C. and stirred for 1 hour. After the reaction was terminated by adding water, the mixture was diluted with ethyl acetate and saturated aqueous potassium sodium tartrate solution were added, followed by 30 minutes of stirring at room temperature. The mixture was extracted with ethyl acetate and the organic layer was washed with saturated brine and then dried over anhydrous sodium sulfate. The solvent was removed by evaporation and the residue was purified by silica gel column chromatography (ethyl acetate/hexane=1/1) to obtain 230 mg of the title compound as colorless powder.

Melting point: 183–184° C.

$^1$H-NMR (CDCl$_3$): δ 1.83 (1H, brs), 2.69 (3H, s), 2.97 (3H, s), 4.69 (2H, d, J=5.7 Hz), 7.47 (1H, dd, J=2.1, 8.7 Hz), 7.57 (1H, dd, J=2.1, 8.7 Hz), 7.74 (1H, d, J=9.3 Hz), 7.78 (1H, d, J=9.3 Hz), 7.79 (1H, d, J=2.1 Hz), 7.86 (1H, d, J=2.1 Hz), 9.49 (1H, brs).

IR $\nu_{max}$ (KBr): 3563, 3236, 1612, 1500, 1392, 1277, 1142 cm$^{-1}$.

Example 14

Synthesis of ethyl 4-(5-chloro-3-methylbenzo[b]thiophene-2-sulfonylamino)benzoate (Compound 14)

Into 3 mL of pyridine was dissolved 60 mg of ethyl 4-aminobenzoate, and 123 mg of 5-chloro-2-chlorosulfonyl-3-methylbenzo[b]thiophene was added at 0° C., followed by 2 hours of stirring at room temperature. After confirmation of disappearance of the starting material, 2 mol/L hydrochloric acid was added, followed by extraction with ether. The organic layer was washed with saturated brine and then dried over anhydrous magnesium sulfate. The solvent was removed by evaporation under reduced pressure and the resulting crude product was purified by silica gel column chromatography (ethyl acetate/hexane=1/3) to obtain 80 mg of the title compound as light pink powder.

Melting point: 224–226° C.

$^1$H-NMR (DMSO-d$_6$): δ 1.26 (3H, t, J=7.1 Hz), 2.50 (3H, s) 4.23 (2H, q, J=7.1 Hz), 7.27 (2H, d, J=8.8 Hz), 7.57 (1H, dd, J=2.0, 8.6 Hz), 7.84 (2H, d, J=8.8 Hz), 8.01 (1H, d, J=2.0 Hz), 8.05 (1H, d, J=8.6 Hz).

IR $\nu_{max}$ (KBr): 3213, 1696, 1608, 1511, 1347, 1288, 1159 cm$^{-1}$.

Example 15

Synthesis of N-(4-benzoylphenyl)-5-chloro-3-methylbenzo[b]thiophene-2-sulfonamide (Compound 15)

In the same manner as in Example 14, 187 mg of the title compound was obtained as colorless powder from 126 mg of 4-benzoylaniline.

Melting point: 198–200° C.

$^1$H-NMR (CDCl$_3$): δ 2.56 (3H, s), 7.22–7.26 (2H, m), 7.44–7.48 (3H, m), 7.55–7.60 (1H, m), 7.70–7.76 (6H, m).

IR ν$_{max}$ (KBr): 3213, 2927, 1724, 1639, 1589, 1508, 1450, 1408, 1288, 1234, 1149 cm$^{-1}$.

Example 16

Synthesis of 5-chloro-N-(2-methanesulfonylphenyl)-3-methylbenzo[b]thiophene-2-sulfonamide (Compound 16)

In the same manner as in Example 14, 52 mg of the title compound was obtained as colorless powder from 100 mg of 2-methanesulfonylaniline.

Melting point: 191–193° C.

$^1$H-NMR (CDCl$_3$): δ 2.68 (3H, s), 3.00 (3H, s), 7.24–7.29 (1H, m), 7.35 (1H, s), 7.74–7.80 (2H, m), 7.46 (1H, dd, J=1.8, 8.6 Hz), 7.74–7.80 (1H, m), 7.85 (1H, dd, J=1.5, 7.9 Hz).

IR ν$_{max}$ (KBr): 3467, 3371, 3228, 3016, 2927, 2858, 1712, 1624, 1566, 1485, 1408, 1288, 1134, 1026 cm$^{-1}$.

Example 17

Synthesis of methyl 4-(5-fluoro-3-methylbenzo[b]thiophene-2-sulfonylamino)-3-methanesulfonylbenzoate (Compound 17)

Into 300 mL of THF was dissolved 14.0 g of methyl 4-amino-3-methanesulfonylbenzoate, followed by addition of 6.10 g of sodium hydride (oily, 60%) at 0° C. After 40 minutes of stirring at the same temperature, 16.0 g of 2-chlorosulfonyl-5-fluoro-3-methylbenzo[b]thiophene was added at 0° C., followed by 3 hours of stirring at room temperature. After confirmation of disappearance of the starting material, the reaction was terminated by adding 2 mol/L hydrochloric acid at 0° C., followed by extraction with ethyl acetate. The organic layer was washed with saturated aqueous sodium hydrogen carbonate solution and saturated brine and then dried over anhydrous sodium sulfate. The solvent was removed by evaporation and the residue was diluted with ethyl acetate. After the solution was treated with active carbon, purification by recrystallization (ethyl acetate/ether) afforded 24.8 g of the title compound as colorless powder.

Melting point: 202–204° C.

$^1$H-NMR (CDCl$_3$): δ 2.69 (3H, s), 3.06 (3H, s), 3.90 (3H, s), 7.28 (1H, ddd, J=2.6, 8.7, 8.9 Hz), 7.46 (1H, dd, J=2.6, 9.2 Hz), 7.76 (1H, dd, J=4.7, 8.9 Hz), 7.87 (1H, d, J=8.8 Hz), 8.19 (1H, dd, J=2.0, 8.8 Hz), 8.50 (1H, d, J=2.0 Hz), 9.83 (1H, s).

IR ν$_{max}$ (KBr): 3182, 1724, 1604, 1504, 1442, 1396, 1346, 1303, 1157 cm$^{-1}$.

Example 18

Synthesis of Methyl 4-(5-methyl-3-methylbenzo[b]thiophene-2-sulfonylamino)-3-methanesulfonylbenzoate (Compound 18)

Into 8.0 mL of THF was dissolved 183 mg of methyl 4-amino-3-methanesulfonylbenzoate, followed by addition of 96 mg of sodium hydride (oily, 60%) at 0° C. After 20 minutes of stirring at the same temperature, 250 mg of 2-chlorosulfonyl-5-methyl-3-methylbenzo[b]thiophene was added at 0° C., followed by 6 hours of stirring at room temperature. After confirmation of disappearance of the starting material, the reaction was terminated by adding 1 mol/L hydrochloric acid at 0° C., followed by extraction with chloroform. The organic layer was washed with saturated brine and then dried over anhydrous sodium sulfate. The solvent was removed by evaporation and then the residue was purified by silica gel column chromatography (ethyl acetate/hexane=3/1 to 1/1) to obtain 181 mg of the title compound as colorless powder.

Melting point: 179–181° C.

$^1$H-NMR (CDCl$_3$): δ 2.48 (3H, s), 2.70 (3H, s), 3.02 (3H, s), 3.89 (3H, s), 7.35 (1H, dd, J=2.2, 8.8 Hz), 7.60 (1H, d, J=2.2 Hz), 7.69 (1H, d, J=8.8 Hz), 7.88 (1H, d, J=8.8 Hz), 8.18 (1H, dd, J=1.8, 8.8 Hz), 8.50 (1H, d, J=1.8 Hz).

IR ν$_{max}$ (KBr): 3460, 3178, 3016, 2927, 2861, 1724, 1604, 1500, 1439, 1396, 1300, 1130, 1061 cm$^{-1}$.

Example 19

Synthesis of N-(4-acetyl-2-methanesulfonylphenyl)-5-fluoro-3-methylbenzo[b]thiophene-2-sulfonamide (Compound 19)

Into a mixed solvent of 168 mL of THF and 42 mL of DMF was dissolved 6.30 g of (4-amino-3-methanesulfonyl)acetophenone, followed by addition of 4.70 g of sodium hydride (oily, 60%) at −40° C. After 10 minutes of stirring at the same temperature, 8.60 g of 2-chlorosulfonyl-5-fluoro-3-methylbenzo[b]thiophene was added at the same temperature, followed by 4 hours of stirring at the same temperature. After confirmation of disappearance of the starting material, the reaction was terminated by adding 1 mol/L hydrochloric acid at the same temperature and then the mixture was rendered pH 1 with concentrated hydrochloric acid, followed by extraction with chloroform. The organic layer was washed with saturated brine and then dried over anhydrous sodium sulfate. The solvent was removed by evaporation and then the residue was diluted with chloroform. After the solution was treated with active carbon, the solvent was removed by evaporation and the resulting crystals were washed with methanol to obtain 10.9 g of the title compound as colorless powder.

Melting point: 174–175° C.

$^1$H-NMR (CDCl$_3$): δ 2.56 (3H, s), 2.69 (3H, s), 3.08 (3H, s), 7.29 (1H, ddd, J=2.5, 8.8, 8.8 Hz), 7.47 (1H, dd, J=2.5, 8.8 Hz), 7.77 (1H, dd, J=4.6, 8.8 Hz), 7.84 (1H, d, J=8.6 Hz), 8.12 (1H, dd, J=2.2, 8.6 Hz), 8.42 (1H, d, J=2.2 Hz), 9.83 (1H, brs).

IR ν$_{max}$ (KBr): 3243, 3092, 3006, 2925, 1672, 1599, 1443, 1392, 1262, 1130, 1056, 1029 cm$^{-1}$.

Example 20

Synthesis of methyl 4-(3-methylbenzo[b]thiophene-2-sulfonylamino)-3-methanesulfonylbenzoate (Compound 20)

Into a mixed solvent of 30 mL of methanol and 30 mL of dioxane was dissolved 640 mg of 5% palladium/carbon, followed by 10 minutes of stirring under a hydrogen atmosphere. Under an argon atmosphere, 330 mg of Compound 1 was added, followed by 3 days of stirring under a hydrogen atmosphere at 5 atm. After confirmation of disappearance of the starting material, the reaction mixture was filtered and purified by silica gel column chromatography (ethyl acetate/hexane=2/1) to obtain 70 mg of the title compound as colorless powder.

Melting point: 170–172° C.

$^1$H-NMR (CDCl$_3$): δ 2.75 (3H, s), 3.04 (3H, s), 3.90 (3H, s), 7.49 (1H, dd, J=7.1, 7.7 Hz), 7.51 (1H, dd, J=7.1, 7.7 Hz), 7.83 (2H, d, J=7.7 Hz), 7.89 (1H, d, J=8.8 Hz), 8.20 (1H, dd, J=2.0, 8.8 Hz), 8.51 (1H, d, J=2.0 Hz), 9.82 (1H, s).

IR ν$_{max}$ (KBr): 3209, 1720, 1604, 1500, 1442, 1392, 1350, 1308, 1165, 1122 cm$^{-1}$.

Example 21

Synthesis of methyl (2S)-2-[4-(5-fluoro-3-methyl-benzo[b]thiophene-2-sulfonylamino)-3-methanesulfonyl]benzoylamino-3-hydroxy-propionate (Compound 21)

Into 450 mL of chloroform was dissolved 14.3 g of the compound of Reference Example 1. After 7.54 g of L-serine methyl ester hydrochloride and 9.30 g of EDC hydrochloride were added thereto at room temperature, 6.80 mL of triethylamine was added at 0° C. After 2 hours of stirring at the same temperature, the reaction was terminated by adding 2 mol/L hydrochloric acid at 0° C. and the mixture was extracted with chloroform. The organic layer was washed with saturated brine and then dried over anhydrous sodium sulfate. The solvent was removed by evaporation and the residue was purified by silica gel column chromatography (ethyl acetate) to obtain 12.9 g of the title compound as colorless amorphous.

$^1$H-NMR (CDCl$_3$): δ 2.71 (3H, s), 3.07 (3H, s), 3.81 (3H, s), 4.00 (1H, dd, J=4.2, 11.4 Hz), 4.15 (1H, dd, J=5.4, 11.4 Hz), 4.85 (1H, dd, J=4.2, 5.4 Hz), 7.33 (1H, dd, J=2.1, 8.6 Hz), 7.48 (1H, dd, J=2.1, 8.6 Hz), 7.79 (1H, dd, J=4.6, 8.6 Hz), 7.87 (1H, d, J=8.8 Hz), 8.00 (1H, dd, J=2.1, 8.8 Hz), 8.32 (1H, d, J=2.1 Hz), 9.76 (1H, s).

IR ν$_{max}$ (KBr): 3401, 1735, 1655, 1606, 1510, 1491, 1440, 1353, 1308, 1164, 1136 cm$^{-1}$.

Example 22

Synthesis of methyl 2-[4-(5-fluoro-3-methylbenzo[b]thiophene-2-sulfonylamiho)-3-methanesulfonylphenyl]-4,5-dihydrooxazole-4-carboxylate (Compound 22)

Into 180 mL of THF was dissolved 12.9 g of Compound 21, and 6.80 g of Burgess reagent (J. Org. Chem., 38, 26, (1973); J. Org. Chem., 58, 4494 (1993)) was added, followed by 2 hours of stirring at 60° C. After confirmation of disappearance of the starting material, the solvent was removed by evaporation and water was added, followed by extraction with ethyl acetate. The organic layer was washed with saturated brine and then dried over anhydrous sodium sulfate. The solvent was removed by evaporation and the residue was purified by silica gel column chromatography (ethyl acetate/hexane=9/1) to obtain 9.92 g of the title compound as colorless amorphous.

$^1$H-NMR (CDCl$_3$): δ 2.68 (3H, s), 3.02 (3H, s), 3.81 (3H, s), 4.60 (1H, dd, J=9.0, 10.6 Hz), 4.69 (1H, dd, J=7.9, 9.0 Hz), 4.93 (1H, dd, J=7.9, 10.6 Hz), 7.29 (1H, ddd, J=2.1, 8.8, 8.8 Hz), 7.46 (1H, dd, J=2.1, 8.8 Hz), 7.76 (1H, dd, J=4.6, 8.8 Hz), 7.87 (1H, d, J=8.8 Hz), 8.15 (1H, dd, J=2.1, 8.8 Hz), 8.43 (1H, d, J=2.1 Hz), 9.81 (1H, s).

IR ν$_{max}$ (KBr): 3226, 1737, 1647, 1608, 1498, 1441, 1395, 1355, 1308, 1248, 1211, 1164 cm$^{-1}$.

Example 23

Synthesis of methyl 2-[4-(5-fluoro-3-methylbenzo[b]thiophene-2-sulfonylamino)-3-methanesulfonylphenyl]oxazole-4-carboxylate (Compound 23)

Into 40 mL of dichloromethane was dissolved 1.10 g of Compound 22, followed by addition of 498 mg of bromotrichloromethane at −20° C. Further, 700 mg of DBU was added dropwise at the same temperature and the whole was stirred at the same temperature for 5 minutes and then warmed to 0° C., followed by 3.5 hours of stirring. After confirmation of disappearance of the starting material, the reaction was terminated by adding saturated aqueous sodium hydrogen carbonate solution at 0° C., followed by extraction with ethyl acetate. The organic layer was washed with saturated brine and then dried over anhydrous magnesium sulfate. The solvent was removed by evaporation and the residue was purified by silica gel column chromatography (ethyl acetate/methanol=20/1) to obtain 597 mg of the title compound as colorless powder.

Melting point: 290–292° C.

$^1$H-NMR (CDCl$_3$): δ 2.70 (3H, s), 3.06 (3H, s), 3.95 (3H, s), 7.30 (1H, ddd, J=2.4, 8.7, 8.7 Hz), 7.47 (1H, dd, J=2.4, 9.0 Hz), 7.77 (1H, dd, J=4.8, 9.0 Hz), 7.94 (1H, d, J=9.0 Hz), 8.27 (1H, s), 8.28 (1H, dd, J=2.1, 9.0 Hz), 8.57 (1H, d, J=2.1 Hz), 9.78 (1H, s).

IR ν$_{max}$ (KBr): 3243, 1720, 1618, 1590, 1518, 1485, 1440, 1355, 1320, 1303, 1259, 1162, 1136 cm$^{-1}$.

Example 24

Synthesis of 2-[4-(5-fluoro-3-methylbenzo[b]thiophene-2-sulfonylamino)-3-methanesulfonylphenyl]oxazole-4-carboxylic acid (Compound 24)

Into 150 mL of methanol was dissolved 7.85 g of Compound 23, and 15 mL of 10% aqueous sodium hydroxide solution and 15 mL of water were added thereto at room temperature, followed by 15 minutes of stirring. The precipitated crystals were dissolved by adding 90 mL of water, and the solution was stirred at the same temperature for 17 hours. After the solvent was removed by evaporation, 45 mL of 1 mol/L hydrochloric acid was added to the residue, the precipitated crystals were collected by filtration and washed with water, and 100 mL of DMF was added to the resulting crude crystals, followed by heating under refluxing. After filtration at a hot state, 70 mL of ethanol was added and recrystallization was carried out. The resulting crystals were collected by filtration, washed several times with ethanol and water alternatively, and dried over diphosphorus pentoxide under reduced pressure to obtain 5.78 g of the title compound as colorless powder.

Melting point: 289–291° C.

$^1$H-NMR (DMSO-$d_6$): δ 2.55 (3H, s), 3.41 (3H, s), 7.44 (1H, ddd, J=1.8, 8.7, 9.0 Hz), 7.64 (1H, d, J=8.4 Hz), 7.79 (1H, dd, J=1.8, 9.9 Hz), 8.08 (1H, dd, J=4.8, 8.7 Hz), 8.19 (1H, dd, J=1.8, 8.4 Hz), 8.41 (1H, d, J=1.8 Hz), 8.84 (1H, s).

IR $v_{max}$ (KBr): 3232, 1717, 1690, 1616, 1487, 1440, 1355, 1313, 1161, 1140 cm$^{-1}$.

Example 25

Synthesis of methyl 2-[4-(5-chloro-3-methylbenzo[b]thiophene-2-sulfonylamino)-3-methanesulfonylphenyl]oxazole-4-carboxylate (Compound 25)

Into 10 mL of dichloromethane was dissolved 495 mg of copper dibromide, followed by addition of 310 mg of hexamethyltetramine at room temperature. Further, 337 mg of DBU was added dropwise at 0° C., the whole was stirred at the same temperature for 5 minutes and then 300 mg of Compound 47 was added at 0° C., followed by 3 hours of stirring at room temperature. After confirmation of disappearance of the starting material, ethyl acetate was added to the reaction mixture. The organic layer was washed with a 1:1 mixed solution of saturated aqueous ammonium chloride solution and 25% aqueous ammonia solution, saturated aqueous sodium hydrogen carbonate and saturated brine and then dried over anhydrous magnesium sulfate. The solvent was removed by evaporation and the residue was purified by silica gel column chromatography (chloroform/methanol=10/1) to obtain 110 mg of the title compound as colorless powder.

Melting point: 237–239° C.

$^1$H-NMR (CDCl$_3$): δ 2.70 (3H, s), 3.05 (3H, s), 3.95 (3H, s), 7.47 (1H, dd, J=2.1, 8.7 Hz), 7.74 (1H, d, J=8.7 Hz), 7.79 (1H, d, J=2.1 Hz), 7.93 (1H, d, J=9.0 Hz), 8.27 (1H, s), 8.28 (1H, dd, J=2.1, 9.0 Hz), 8.56 (1H, d, J=2.1 Hz), 9.72 (1H, brs).

IR $v_{max}$ (KBr): 3231, 1744, 1486, 1317, 1136 cm$^{-1}$.

Example 26

Synthesis of 2-[4-(5-chloro-3-methylbenzo[b]thiophene-2-sulfonylamino)-3-methanesulfonylphenyl]oxazole-4-carboxylic acid (Compound 26)

In the same manner as in Example 24, 68 mg of the title compound was obtained as colorless powder from 70 mg of Compound 25.

Melting point: 296–298° C.

$^1$H-NMR (DMSO-$d_6$): δ 2.58 (3H, s), 3.37 (3H, s), 7.55 (1H, dd, J=2.1, 8.7 Hz), 7.62 (1H, d, J=8.7 Hz), 8.01 (1H, d, J=2.1 Hz), 8.09 (1H, d, J=8.4 Hz), 8.12 (1H, dd, J=2.1, 8.4 Hz), 8.40 (1H, d, J=2.1 Hz), 8.83 (1H, s).

IR $v_{max}$ (KBr): 3221, 2924, 1701, 1485, 1311, 1153 cm$^{-1}$.

Example 27

Synthesis of disodium 2-[4-(5-fluoro-3-methylbenzo[b]thiophene-2-sulfonylamino)-3-methanesulfonylphenyl]oxazole-4-carboxylate (Compound 27)

Into 30 mL of methanol was dissolved 290 mg of Compound 23, followed by addition of 77 mg of sodium methoxide. After 8 hours of stirring at room temperature, ether was added and the precipitated crystals were collected by filtration and washed with ether to obtain 300 mg of the title compound as colorless powder.

Melting point: 341–343° C.

$^1$H-NMR (DMSO-$d_6$): δ 2.49 (3H, s), 3.42 (3H, s), 7.26 (1H, ddd, J=2.4, 8.8, 9.0 Hz), 7.40 (1H, dd, J=9.0, 9.0 Hz), 7.56 (1H, dd, J=2.4, 8.9 Hz), 7.89 (1H, dd, J=2.2, 9.0 Hz), 7.95 (1H, d, J=9.0 Hz), 8.19 (1H, d, J=2.2 Hz).

IR $v_{max}$ (KBr): 3490, 1609, 1570, 1523, 1470, 1441, 1400, 1302, 1280, 1119 cm$^{-1}$.

In the following, Compounds 28 to 49 of Examples 28 to 49 were synthesized in the same manner as in Example 1.

TABLE 1

(I)

| Example | $R^1$ | $R^2$ | $R^3$ | $R^4$ | $R^5$ |
|---|---|---|---|---|---|
| 28 | Cl | Me | H | $NO_2$ | H |
| 29 | Cl | Me | H | CN | H |
| 30 | Cl | Me | H | COMe | H |
| 31 | Cl | Me | H | $CONH_2$ | H |
| 32 | Cl | Me | H | $COCH_2SCH_2CO_2Me$ | H |
| 33 | Cl | Me | OMe | $NO_2$ | H |
| 34 | Cl | Me | $NO_2$ | CN | H |
| 35 | Cl | Me | $NO_2$ | $NO_2$ | H |
| 36 | Cl | Me | $NO_2$ | OMe | H |
| 37 | Cl | Me | OMe | $CONHCH_2CO_2Et$ | H |
| 38 | Cl | Me | $CO_2Me$ | OMe | OMe |
| 39 | Cl | Me | H | $SO_2(CH_2)_2CH_3$ | H |
| 40 | H | Me | H | $SO_2(CH_2)_2CH_3$ | H |
| 41 | Me | Me | H | $SO_2(CH_2)_2CH_3$ | H |
| 42 | Cl | Me | $SO_2Me$ | $CO_2CH(CH_3)_2$ | H |
| 43 | Cl | Me | $SO_2Me$ | $CONHCH_2CO_2Et$ | H |
| 44 | Cl | Me | $SO_2Me$ | HN–CH(CH$_2$OH)–C(O)–, $CO_2Me$ substituent | H |

TABLE 2

(I)

| Example | $R^1$ | $R^2$ | $R^3$ | $R^4$ | $R^5$ |
|---|---|---|---|---|---|
| 45 | Cl | Me | $SO_2Me$ | HN–CH(CH$_2$CH$_2$SMe)–C(O)–, $CO_2Me$ substituent | H |

TABLE 2-continued (I) Structure: R¹-benzothiophene with R², SO₂NH-phenyl(R³, R⁴, R⁵)

| Example | R¹ | R² | R³ | R⁴ | R⁵ |
|---------|----|----|----|----|----|
| 46 | Cl | Me | SO₂Me | (pyrrolidine-N-C(O)- with CO₂Me) | H |
| 47 | Cl | Me | SO₂Me | (oxazoline with CO₂Me) | H |
| 48 | F | Me | SO₂Me | (oxazole) | H |
| 49 | F | Me | SO₂NEt₂ | CO₂Me | H |

Example 50

Synthesis of 2-[4-(5-chloro-3-methylbenzo[b]thiophene-2-sulfonylamino)-3-methoxybenzoylamino]acetic Acid (Compound 50)

Into 25 mL of ethanol was dissolved 104 mg of Compound 37, and 1 mL of 1 mol/L aqueous sodium hydroxide solution was added at room temperature, followed by 15 hours of stirring at the same temperature. After confirmation of disappearance of the starting material, the solvent was removed by evaporation, followed by extraction with ether. After 2 mol/L hydrochloric acid was added to the aqueous layer, the mixture was extracted with ethyl acetate. The organic layer was washed with saturated brine and then dried over anhydrous sodium sulfate. The solvent was removed by evaporation and the resulting powder was washed with ether to obtain 97 mg of the title compound as light yellow powder.

Melting point: 282–285° C.

$^1$H-NMR (CDCl$_3$/CD$_3$OD): δ 2.50 (3H, s), 3.82 (2H, s), 3.84 (3H, s), 7.10–7.15 (2H, m), 7.20–7.35 (2H, m), 7.60–7.70 (2H, m).

IR vv$_{max}$ (KBr): 3394, 2974, 1604, 1554, 1493, 1412, 1284, 1230, 1130 c m$^{-1}$.

Example 51

Synthesis of sodium methyl 4-(5-chloro-3-methylbenzo[b]thiophene-2-sulfonylamino)-3-methanesulfonylbenzoate (Compound 51)

Into 8 mL of THF was dissolved 115 mg of Compound 1, followed by addition of 15 mg of sodium hydride (oily, 60%) at room temperature. After 1.5 hours of stirring at the same temperature, the solvent was removed by evaporation and the resulting powder was washed with ether to obtain 61 mg of the title compound as colorless powder.

Melting point: >300° C.

$^1$H-NMR (DMSO-d$_6$): δ 2.51 (3H, s), 3.37 (3H, s), 3.72 (3H, s), 7.39 (1H, d, J=2.1, 8.8 Hz), 7.40 (1H, dd, J=10.8, 8.5 Hz), 7.68 (1H, dd, J=1.8, 8.8 Hz), 7.80 (1H, d, J=1.8 Hz), 7.93 (1H, d, J=8.5 Hz), 8.23 (1H, d, J=1.8 Hz).

IR v$_{max}$ (KBr): 3448, 1705, 1597, 1481, 1442, 1292, 1134, 1103 cm$^{-1}$.

After Compound 43, 44 and 46 were subjected to ester hydrolysis, the products were converted into sodium salts in the same conditions as in Example 51 to synthesize Compounds 52, 53 and 54 of Examples 52, 53 and 54.

TABLE 3

(I)

| Example | R¹ | R² | R³ | R⁴ | R⁵ |
|---------|----|----|----|----|----|
| 52 | Cl | Me | SO₂Me | CONHCH₂CO₂Na | H |
| 53 | Cl | Me | SO₂Me | (NH-CH(CH₂OH)-C(O)- with CO₂Na) | H |
| 54 | Cl | Me | SO₂Me | (pyrrolidine-N-C(O)- with CO₂Na) | H |

The following show instrumental data in each Examples.

TABLE 4

| Example | Melting point (° C.) | H¹-NMR (δ) | | IR (v cm$^{-1}$, KBr) |
|---------|---------------------|------------|--|----------------------|
| 28 | Amorphous | CDCl₃ | 2.62(3H, s), 7.29 (2H, d, J = 9.1 Hz), 7.46(1H, dd, J = 2.0, 8.7 Hz), 7.47 (1H, brs), 7.73(1H, d, J = 8.7 Hz), 7.76(1H, d, J = 2.0 Hz), 8.15(2H, d, J = 9.1 Hz) | 3248, 3084, 2925, 2856, 1596, 1521, 1342, 1160, 1113 |
| 29 | 226–227 | CDCl₃/ CD₃OD | 2.60(3H, s), 7.29 (2H, d, J = 9.0 Hz), 7.45(1H, dd, J = 2.1, 8.7 Hz), 7.53 (2H, d, J = 9.0 Hz), 7.75(1H, d, J = 2.1 Hz), 7.76–7.77 (1H, m) | 3236, 2222, 1606, 1508, 1469, 1356, 1160 |
| 30 | 223–225 | CDCl₃ | 2.53(3H, s), 2.54 (3H, s), 7.20–7.23 (2H, m), 7.45(1H, | 3178, 2927, 2233, 1666, 1593, 1508, |

TABLE 4-continued

| Example | Melting point (° C.) | H¹-NMR (δ) | IR (ν cm⁻¹, KBr) |
|---|---|---|---|
| | | | dd, J = 2.1, 8.6 Hz), 7.72(2H, d, J = 8.6 Hz), 7.88(2H, d, 8.6 Hz) | 1404, 1338, 1273, 1153 |
| 31 | 254–258 | CDCl₃ | 2.55(3H, s), 7.24 (2H, d, J = 7.4 Hz), 7.36–7.45(3H, m), 7.72(2H, d, J = 8.6 Hz) | 3379, 3255, 3174, 2911, 2846, 2765, 1651, 1512, 1404, 1335, 1223, 1157 |
| 32 | 151–153 | CDCl₃ | 2.57(3H, s), 3.30 (2H, s), 3.71(3H, s), 3.93(2H, s), 7.20–7.25(2H, m), 7.44–7.47(1H, m), 7.71–7.75(2H, m), 7.86–7.90(2H, m) | 3221, 3059, 2935, 1736, 1662, 1593, 1512, 1466, 1404, 1338, 1296, 1153 |
| 33 | 188–190 | CDCl₃ | 2.63(3H, s), 3.92 (3H, s), 7.45(1H, dd, J = 2.0, 8.8 Hz), 7.63(1H, brs), 7.67 (1H, d, J = 2.4 Hz), 7.71(1H, d, J = 8.8 Hz), 7.76(1H, d, J = 2.0 Hz), 7.84(1H, dd, J = 2.4, 8.8 Hz) | 3293, 3088, 2930, 2846, 1735, 1596, 1525, 1500, 1442, 1402, 1342, 1281, 1254, 1163, 1130 |

TABLE 5

| Example | Melting point (° C.) | H¹-NMR (δ) | IR (ν cm⁻¹, KBr) |
|---|---|---|---|
| 34 | 204–206 | CDCl₃ | 2.71(3H, s), 7.51 (1H, dd, J = 2.0, 8.6 Hz), 7.76(1H, d, J = 8.6 Hz), 7.83 (1H, dd, J = 2.0, 8.8 Hz), 7.85(1H, d, J = 2.0 Hz), 8.12 (1H, d, J = 8.8 Hz), 8.51(1H, d, J = 2.0 Hz) | 3234, 3081, 2923, 2235, 1620, 1561, 1538, 1499, 1415, 1360, 1324, 1278, 1164, 1145, 1113 |
| 35 | 162–164 | CDCl₃ | 2.71(3H, s), 7.50 (1H, dd, J = 2.0, 8.6 Hz), 7.74(1H, d, J = 8.6 Hz), 7.80(1H, d, J = 2.0 Hz), 8.15 (1H, d, J = 9.4 Hz), 8.43(1H, dd, J = 2.5, 9.4 Hz), 9.08 (1H, d, J = 2.5 Hz) | 3398, 3232, 1604, 1493, 1423, 1346, 1165 |
| 36 | 120–122 | CDCl₃ | 2.52(3H, s), 3.82 (3H, s), 7.18–7.22(1H, m), 7.42–7.50(2H, m), 7.67–7.73(2H, m), 7.88 (1H, d, J = 9.2 Hz) | 3325, 3078, 2931, 2838, 1905, 1619, 1523, 1439, 1346, 1265, 1153 |
| 37 | 196–198 | CDCl₃ | 1.30(3H, t, J = 7.2 Hz), 2.55(3H, s), 3.77(3H, s), 4.18 (2H, d, J = 4.9 Hz), 4.25(2H, q, J = 7.2 Hz), 7.33(1H, d, J = 1.8 Hz), 7.40–7.45(2H, m), 7.60–7.75(3H, m) | 3278, 1743, 1639, 1550, 1508, 1408, 1350, 1215, 1165 |
| 38 | 203–205 | CDCl₃ | 2.56(3H, s), 3.82 (6H, s), 3.96(3H, s), 7.30(1H, s), 7.41 (1H, s), 7.39–7.44 (1H, m), 7.67(1H, s), 7.68–7.75(1H, m) | 3444, 3170, 2947, 1678, 1612, 1520, 1442, 1362, 1257, 1207, 1161 |

TABLE 5-continued

| Example | Melting point (° C.) | H¹-NMR (δ) | IR (ν cm⁻¹, KBr) |
|---|---|---|---|
| 39 | 181–183 | CDCl₃ | 0.96(3H, t, J = 7.6 Hz), 1.69(2H, sext, J = 7.6 Hz), 2.58 (3H, s), 3.00(2H, t, J = 7.6 Hz), 7.31 (2H, d, J = 8.8 Hz), 7.47(1H, dd, J = 2.1, 8.7 Hz), 7.72 (1H, d, J = 8.7 Hz), 7.74(1H, d, J = 2.1 Hz), 7.79(2H, d, J = 8.8 Hz) | 3217, 2966, 1593, 1493, 1404, 1350, 1288, 1238, 1142, 1088 |

TABLE 6

| Example | Melting point (° C.) | H¹-NMR (δ) | IR (ν cm⁻¹, KBr) |
|---|---|---|---|
| 40 | 201–203 | CDCl₃ | 0.95(3H, t, J = 7.9 Hz), 1.66(2H, sext, J = 7.9 Hz), 2.67 (3H, s), 3.05(2H, t, J = 7.9 Hz), 7.40 (2H, d, J = 9.0 Hz), 7.47(1H, td, J = 1.5, 7.9 Hz), 7.51(1H, td, J = 1.5, 7.9 Hz), 7.74(2H, d, J = 9.0 Hz), 7.84(2H, dt, J = 1.5, 7.9 Hz) | 3195, 3058, 2930, 2878, 1594, 1497, 1489, 1346, 1281, 1160, 1132 |
| 41 | 201–203 | CDCl₃ | 0.96 (3H, t, J = 7.7 Hz), 1.69(2H, sext, J = 7.7 Hz), 2.49 (3H, s), 2.59(3H, s), 3.00(2H, t, J = 7.7 Hz), 7.11(1H, s), 7.30(2H, d, J = 8.6 Hz), 7.34(1H, d, J = 8.4 Hz), 7.56(1H, s), 7.68(1H, d, J = 8.4 Hz), 7.78(2H, d, J = 8.6 Hz) | 3194, 3059, 2962, 2877, 1593, 1493, 1400, 1342, 1292, 1138 |
| 42 | 164–166 | CDCl₃ | 1.33(6H, d, J = 6.2 Hz), 2.70 (3H, s), 3.06(3H, s), 5.22(1H, q, 6.2 Hz), 7.47(1H, dd, J = 2.1, 8.8 Hz), 7.74 (1H, d, J = 8.8 Hz), 7.79(1H, d, J = 1.5 Hz), 7.85(1H, d, J = 8.6 Hz), 8.18(1H, d, J = 8.6 Hz), 8.48 (1H, d, J = 1.5 Hz), 9.82(1H, s) | 3410, 3244, 2924, 1709, 1604, 1500, 1350, 1304, 1153 |
| 43 | 88–90 | CD₃OD | 1.25(3H, t, J = 7.2 Hz), 2.64(3H, s), 3.19(3H, brs), 4.05 (2H, s), 4.17(2H, q, J = 7.2 Hz), 7.45 (1H, d, J = 8.7 Hz), 7.75(1H, brd, J = 6.9 Hz), 7.85(1H, d, J = 8.7 Hz), 7.87 (1H, s), 7.96(1H, brd, J = 6.9 Hz), 8.34(1H, d, J = 1.8 Hz) | 3359, 3232, 3078, 2989, 2927, 1739, 1655, 1604, 1485, 1304, 1211, 1161, 1134 |

TABLE 7

| Example | Melting point (° C.) | | H¹-NMR (δ) | IR (ν cm⁻¹, KBr) |
|---|---|---|---|---|
| 44 | 154–156 | CD₃OD | 2.65(3H, s,), 3.07 (3H, s), 3.73(3H, s), 3.89(1H, dd, J = 4.2 Hz, 11.4 Hz), 3.95 (1H, dd, J = 5.4, 11.4 Hz), 4.68(1H, dd, J = 4.2, 5.4 Hz), 7.47(1H, dd, J = 2.1, 8.4 Hz), 7.85 (2H, dd, J = 2.1, 8.7 Hz), 7.91(H, d, J = 2.1 Hz), 8.09 (1H, dd, J = 2.1, 8.7 Hz), 8.36(1H, d, J = 2.1 Hz) | 3220, 2924, 1736, 1643, 1608, 1496, 1303, 1161, 1130 |
| 45 | Amorphous | CDCl₃ | 2.10(3H, s), 2.20 (2H, m), 2.56(2H, m), 2.70(3H, s), 3.05(3H, s), 3.78 (3H, s), 4.89(1H, m), 7.09(1H, brs), 7.48(1H, brm), 7.87 (2H, m), 7.96(1H, m), 8.29(1H, brs), 9.73(1H, brs) | 3230, 2921, 2853, 1739, 1653, 1604, 1541, 1492, 1440, 1393, 1353, 1307, 1226, 1166, 1131, 1105 |
| 46 | Amorphous | CDCl₃ | 2.00–2.30(4H, m), 2.70(3H, s), 2.98 (3H, s), 3.50–3.65 (2H, m), 3.76(3H, s), 4.61(1H, m), 7.48(1H, d, J = 8.4 Hz), 7.75(1H, d, J = 8.4 Hz), 7.70–7.80 (3H, m), 8.10(1H, s) 9.69(1H, brs) | 3228, 2952, 2925, 1741, 1631, 1496, 1423, 1390, 1353, 1308, 1281, 1203, 1167, 1133, 1107, 1080 |
| 47 | Amorphous | CDCl₃ | 2.69(3H, s), 3.01 (3H, s), 3.80(3H, s,), 4.58(1H, dd, J = 9.0, 10.5 Hz), 4.68 (1H, dd, J = 8.1, 9.0 Hz), 4.93(1H, dd, J = 8.1, 10.5 Hz), 7.47(1H, dd, J = 2.1, 8.4 Hz), 7.73(1H, d, J = 8.4 Hz), 7.78(1H, d, J = 2.1 Hz), 7.86(1H, d, J = 8.7 Hz), 8.14 (1H, dd, J = 2.1, 8.7 Hz), 8.43(1H, d, J = 2.1 Hz) | 3224, 2958, 1739, 1500, 1308, 1161 |

TABLE 8

| Example | Melting point (° C.) | | H¹-NMR (δ) | IR (ν cm⁻¹, KBr) |
|---|---|---|---|---|
| 48 | 199–201 | DMSO-d₆ | 2.51(3H, s,), 3.17 (3H, s), 7.46(1H, ddd, J = 1.8, 9.0, 9.0 Hz), 7.52(1H, d, J = 8.4 Hz), 7.75 (1H, d, J = 1.8 Hz), 7.81 (1H, dd, J = 1.8, 8.7 Hz), 7.98 (1H, dd, J = 1.8, 8.4 Hz), 8.10(1H, dd, J = 4.8, 9.0 Hz), 8.15(1H, s), 8.48 (1H, s) | 3243, 3119, 1606, 1501, 1303, 1151 |
| 49 | 137–140 | CDCl₃ | 1.14(6H, t, J = 7.1 Hz), 2.68(3H, s), 3.31(4H, q, J = 7.1 Hz), 3.88(3H, s), 7.29(1H, ddd, J = 2.1, 8.8, 8.8 Hz), 7.45 (1H, dd, J = 2.1, 8.8 Hz), 7.75(1H, dd, J = 4.8, 8.8 Hz), 7.84 (1H, d, J = 8.6 Hz), 8.07(1H, dd, J = 2.0, 8.6 Hz), 8.35 (1H, d, J = 2.0 Hz), 9.88(1H, s) | 3157, 3076, 2979, 2949, 1727, 1604, 1577, 1560, 1521, 1498, 1473, 1458, 1438, 1389, 1344, 1325, 1307, 1280, 1200, 1159, 1134, 1100 |
| 52 | 290–292 | D₂O | 2.50(3H, s), 3.47 (3H, s), 3.82(2H, s), 7.22(1H, d, J = 8.7 Hz), 7.42(1H, dd, J = 1.8, 8.7 Hz), 7.69(1H, dd, J = 2.1, 8.7 Hz), 7.80 (1H, d, J = 8.7 Hz), 7.83(1H, d, J = 2.1 Hz), 8.21(1H, d, J = 1.8 Hz) | 3410, 1600, 1473, 1400, 1296, 1134, 1107 |
| 53 | 260 | D₂O | 2.47(3H, s), 3.48 (3H, s), 3.81(1H, dd, J = 5.7 Hz, 11.4 Hz), 3.87(1H, dd, J = 3.6, 11.4 Hz), 4.38(1H, dd, J = 3.6, 5.7 Hz), 7.24 (1H, d, 8.7 Hz), 7.33(1H, d, J = 8.7 Hz), 7.68–7.73(3H, m), 8.24(1H, d, J = 2.1 Hz) | 3464, 1597, 1473, 1408, 1292, 1134, 1107 |

TABLE 9

| Example | Melting point (° C.) | | H¹-NMR (δ) | IR (ν cm⁻¹, KBr) |
|---|---|---|---|---|
| 54 | 298 | D₂O | 1.66–1.78(2H, m), 2.06–2.12(2H, m), 2.32(3H, s), 3.43 (3H, s), 3.37–3.48 (2H, m), 4.14(1H, m), 6.99(1H, d, J = 8.7 Hz), 7.10–7.25(2H, m), 7.34–7.40(2H, m), 7.51(1H, d, J = 8.7 Hz), 7.95(1H, d, J = 1.8 Hz) | 3419, 1599, 1436, 1308, 1105 |

Example 55

Synthesis of 5-fluoro-N-[2-methanesulfonyl-4-(5-methoxy-4-methylthiazol-2-yl)phenyl]-3-methyl-benzo[b]thiophene-2-sulfonamide (Compound 55)

Under an argon atmosphere, 41 mg of 2-methanesulfonyl-4-(5-methoxy-4-methylthiazol-2-yl)aniline was dissolved into a mixed solution of 3 mL of THF and 3 mL of dimethylacetamide. The solution was cooled to −25° C. and 15 mg of sodium hydride (oily, 60%) was added thereto, followed by 10 minutes of stirring at the same temperature. Further, 44 mg of 2-chlorosulfonyl-5-fluoro-3-methylbenzo[b]thiophene was added and the whole was stirred for 2 hours at the same temperature, followed by termination of the reaction with 1 mol/L hydrochloric acid. After the reaction mixture was warmed to room temperature, the mixture was extracted with ethyl acetate-toluene (2/1) and the organic layer was washed with water and saturated brine, successively. After the organic layer was dried over anhydrous sodium sulfate, the solvent was removed by evaporation under reduced pressure and the resulting residue was purified by silica gel column chromatography (ethyl acetate/hexane=1/1) to obtain 51 mg of the title compound as light yellow powder.

Melting point: 216–217° C.

$^1$H-NMR (CDCl$_3$): δ 2.29 (3H, s), 2.68 (3H, s), 2.99 (3H, s), 3.93 (3H, s), 7.27 (1H, ddd, J=2.6, 8.6, 8.8 Hz), 7.46 (1H, dd, J=2.6, 9.2 Hz), 7.75 (1H, dd, J=4.7, 8.8 Hz), 7.82 (1H, d, J=8.7 Hz), 7.96 (1H, dd, J=2.1, 8.7 Hz), 8.25 (1H, d, J=2.1 Hz), 9.57 (1H, s).

IR ν$_{max}$ (KBr): 3202, 2989, 2910, 1604, 1558, 1501, 1441, 1349, 1298, 1253, 1156, 1133, 926 cm$^{-1}$.

Example 56

Synthesis of 5-fluoro-N-[2-methanesulfonyl-4-(5-methoxy-4-methyloxazol-2-yl)phenyl]-3-methyl-benzo[b]thiophene-2-sulfonamide (Compound 56)

Into 26 mL of phosphorus oxychloride was added 5.28 g of the compound of Reference Example 2, followed by 3 hours of heating under refluxing. After the reaction mixture was cooled to room temperature, the mixture was poured into ice and extracted with chloroform. The organic layer was washed with water and saturated brine, successively and dried over anhydrous sodium sulfate. The solvent was removed by evaporation under reduced pressure and the resulting residue was purified by silica gel column chromatography (chloroform) to obtain 2.02 g of the title compound as colorless powder.

Melting point: 232–233° C.

$^1$H-NMR (DMSO-d$_6$): δ 2.02 (3H, s), 2.57 (3H, s), 3.32 (3H, s), 3.96 (3H, s), 7.46 (1H, ddd, J=2.5, 9.0, 9.0 Hz), 7.54 (1H, d, J=8.4 Hz), 7.81 (1H, dd, J=2.5, 9.9 Hz), 8.06 (1H, dd, J=1.9, 8.4 Hz), 8.10 (1H, dd, J=4.9, 9.0 Hz), 8.26 (1H, d, J=1.9 Hz).

IR ν$_{max}$ (KBr): 3253, 3083, 3000, 2922, 1665, 1491, 1442, 1393, 1354, 1308, 1169, 1131 cm$^{-1}$.

Example 57

Synthesis of 5-fluoro-N-[2-methanesulfonyl-4-(5-methylthiazol-2-yl)phenyl]-3-methylbenzo[b]thiophene-2-sulfonamide (Compound 57)

Into 5 mL of 1,4-dioxane solution of 150 mg of 4-(5-fluoro-3-methylbenzo[b]thiophene-2-yl)sulfonamido-3-methanesulfonyl-N-(2-oxopropyl)benzamide was added 135 mg of diphosphorus pentasulfide, followed by 4.5 hours of heating under refluxing. The reaction was terminated by adding water to the reaction mixture and the mixture was extracted with ethyl acetate. The organic layer was washed with water and saturated brine, successively and then dried over anhydrous sodium sulfate. The solvent was removed by evaporation under reduced pressure and the resulting residue was purified by silica gel column chromatography (hexane/ethyl acetate 2/1 to 1/1) to obtain 115 mg of the title compound as amorphous.

$^1$H-NMR (CDCl$_3$): 2.51 (3H, s), 2.69 (3H, s), 3.02 (3H, s), 7.27 (1H, ddd, J=2.4, 8.6, 8.9 Hz), 7.47 (1H, dd, J=2.4, 9.2 Hz), 7.50 (1H, s), 7.76 (1H, dd, J=4.8, 8.9 Hz), 7.86 (1H, d, J=8.8 Hz), 8.05 (1H, dd, J=2.1, 8.8 Hz), 8.35 (1H, d, J=2.1 Hz), 9.64 (1H, s).

IR ν$_{max}$ (KBr): 3240, 3010, 2926, 1607, 1499, 1353, 1302, 1160, 994 cm$^{-1}$.

In the following, the compounds 58 to 62 of Examples 58 to 62 were synthesized in the same manner as in Examples 56 and 57.

TABLE 10

(I)

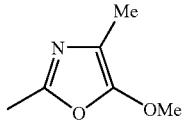

| Example | R$^1$ | R$^2$ | R$^3$ | R$^4$ | R$^5$ |
|---------|-------|-------|-------|-------|-------|
| 58 | Cl | Me | SO$_2$Me | 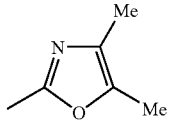 | H |
| 59 | F | Me | SO$_2$Me | 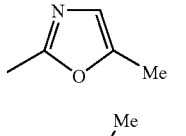 | H |
| 60 | F | Me | SO$_2$Me | 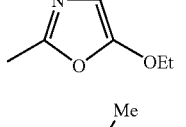 | H |
| 61 | F | Me | SO$_2$Me | (see structure) | H |
| 62 | F | Me | SO$_2$Me | (see structure) | H |

Example 63

Synthesis of 5-fluoro-N-[4-(4-hydroxymethylthiazol-2-yl)-2-methanesulfonylphenyl]-3-methylbenzo[b]thiophene-2-sulfonamide (Compound 63)

Into 226 mL of THF suspension of 298 mg of lithium aluminum hydride was added dropwise 452 mL of THF solution of 4.52 g of Compound 69, followed by 6 hours of stirring at room temperature. Further, 298 mg of lithium aluminum hydride was added thereto, followed by 14 hours of stirring at room temperature. After confirmation of disappearance of the starting material, the reaction was terminated by adding 10 mL of water at 10° C. and the mixture was stirred for 30 minutes. The solvent was removed by evaporation under reduced pressure and chloroform was added to the resulting residue. The organic layer was washed with 1 mol/L sulfuric acid, water and saturated brine, successively and then dried over anhydrous sodium sulfate. The solvent was removed by evaporation under reduced pressure and the resulting residue was purified by silica gel column chromatography (ethyl acetate/hexane=1/1). To the resulting crystals were added 140 mL of chloroform and 28 mL of hexane, followed by heating under refluxing. After filtration at a hot state, the crystals obtained by recrystallization were collected by filtration and dried under reduced pressure to obtain 2.58 g of the title compound as light yellow powder.

Melting point: 209–210° C.

$^1$H-NMR (CDCl$_3$): δ 2.69 (3H, s), 3.04 (3H, s), 4.80 (2H, s), 7.22 (1H, s), 7.27 (1H, ddd, J=2.4, 8.6, 8.8 Hz), 7.47 (1H, dd, J=2.4, 9.2 Hz), 7.76 (1H, dd, J=4.7, 8.8 Hz), 7.88 (1H, d, J=8.8 Hz), 8.09 (1H, dd, J=2.2, 8.8 Hz), 8.42 (1H, d, J=2.2 Hz), 9.65 (1H, s).

IR $ν_{max}$ (KBr): 3423, 3237, 3114, 3026, 2930, 1605, 1509, 1445, 1354, 1294, 1152, 1135 cm$^{-1}$.

Example 64

Synthesis of N-[4-(4-chloromethylthiazol-2-yl)-2-methanesulfonylphenyl]-5-fluoro-3-methylbenzo[b]thiophene-2-sulfonamide (Compound 64)

Into 20 mL of chloroform was suspended 159 mg of Compound 63, and 47 μL of thionyl chloride was added at 0° C., followed by 21 hours of stirring at room temperature. Further, 1 mL of thionyl chloride was added, followed by 1 hour of heating under refluxing. After 2 mL of triethylamine was added at 0° C. and the mixture was stirred for 3 hours, the reaction was terminated with 1 mol/L hydrochloric acid, followed by extraction with ethyl acetate. The organic layer was washed with water and saturated brine, successively and then dried over anhydrous sodium sulfate. The solvent was removed by evaporation under reduced pressure and the resulting residue was purified by silica gel column chromatography (chloroform) to obtain 104 mg of the title compound as light brown powder.

Melting point: 190–191° C.

$^1$H-NMR (CDCl$_3$): δ 2.69 (3H, s), 3.04 (3H, s), 4.70 (2H, s), 7.28 (1H, ddd, J=2.5, 8.6, 8.8 Hz), 7.34 (1H, s), 7.47 (1H, dd, J=2.5, 9.2 Hz), 7.76 (1H, dd, J=4.7, 8.8 Hz), 7.89 (1H, d, J=8.8 Hz), 8.11 (1H, dd, J=2.2, 8.8 Hz), 8.41 (1H, d, J=2.2 Hz), 9.66 (1H, s).

IR $ν_{max}$ (KBr): 3236, 3098, 3027, 2927, 1607, 1507, 1457, 1354, 1306, 1156, 1137, 912 cm$^{-1}$.

Example 65

Synthesis of 5-fluoro-N-[2-methanesulfonyl-4-(4-methylthiazol-2-yl)phenyl]-3-methylbenzo[b]thiophene-2-sulfonamide (Compound 65)

Into 10 mL of acetone was dissolved 64 mg of Compound 64, and 180 mg of sodium iodide was added, followed by 24 hours of heating under refluxing. Further, 180 mg of sodium iodide was added and the mixture was heated under refluxing for 19 hours. The solvent was removed by evaporation under reduced pressure and the residue was dissolved into ethyl acetate. The solution was washed with water, 5% aqueous sodium thiosulfate solution, water and saturated brine, successively, and then dried over anhydrous sodium sulfate. After the solvent was removed by evaporation under reduced pressure, the resulting 5-fluoro-N-[4-(4-iodomethylthiazol-2-yl)-2-methanesulfonylphenyl]-3-methylbenzo[b]thiophene-2-sulfonamide was dissolved into a mixed solution of 5 mL of toluene and 0.5 mL of DMSO, and 45 μL of tributyltin hydride and 13 μL of 1.06 mol/L hexane solution of triethylboron were added, followed by 6 hours of stirring at room temperature. Further, 24 μl of tributyltin hydride was added and the mixture was stirred at room temperature for 3 hours. Then, the reaction was terminated by adding saturated aqueous ammonium chloride solution, followed by extraction with ethyl acetate. The organic layer was washed with water and saturated brine, successively, and then dried over anhydrous sodium sulfate. The solvent was removed by evaporation under reduced pressure and the resulting residue was purified by silica gel column chromatography (hexane to hexane/ethyl acetate=3/1) to obtain 29 mg of the title compound as colorless powder.

Melting point: 199–200° C.

$^1$H-NMR (CDCl$_3$): δ 2.48 (3H, s), 2.69 (3H, s), 3.03 (3H, s), 6.91 (1H, s), 7.27 (1H, ddd, J=2.4, 8.6, 8.8 Hz), 7.46 (1H, dd, J=2.4, 9.2 Hz), 7.75 (1H, dd, J=4.7, 8.8 Hz), 7.87 (1H, d, J=8.7 Hz), 8.09 (1H, dd, J=2.1, 8.7 Hz), 8.40 (1H, d, J=2.1 Hz), 9.65 (1H, s).

IR $ν_{max}$ (KBr): 3243, 3105, 3028, 2925, 1607, 1508, 1442, 1355, 1308, 1162, 1135, 913 cm$^{-1}$.

In the following, Compounds 66 to 68 of Examples 66 to 68 were synthesized in the same manner in Examples 63 to 65.

TABLE 11

(I)

[Structure: R$^1$-substituted benzo[b]thiophene-2-sulfonamide with R$^2$, R$^3$, R$^4$, R$^5$ substituents on phenyl ring]

| Example | R$^1$ | R$^2$ | R$^3$ | R$^4$ | R$^5$ |
|---------|-------|-------|-------|-------|-------|
| 66 | F | Me | SO$_2$Me | 2-methyloxazol-4-yl-CH$_2$OH | H |
| 67 | F | Me | SO$_2$Me | 2-methyloxazol-4-yl-CH$_2$Cl | H |
| 68 | F | Me | SO$_2$Me | 2,4-dimethyloxazol-4-yl | H |

Example 69

Synthesis of methyl 2-[4-(5-fluoro-3-methylbenzo[b]thiophene-2-sulfonylamino)-3-methanesulfonylphenyl]thiazole-4-carboxylate (Compound 69)

Into 204 mL of dichloromethane was dissolved 11.06 g of Compound 74, followed by dropwise addition of 2.4 mL of bromotrichloromethane at 0° C. over the period of 5 minutes. After 20 minutes of stirring at the same temperature, 7.6 mL of DBU was added dropwise over the period of 15 minutes. After the mixture was stirred at room temperature for 5 minutes, the reaction was terminated with 1 mol/L hydrochloric acid. The organic layer was separated, washed with water and saturated brine, and then dried over anhydrous sodium sulfate. The solvent was removed by evaporation under reduced pressure and the resulting residue was purified by silica gel column chromatography (chloroform) to obtain 9.18 g of the title compound as colorless powder.

Melting point: 241–242° C.

$^1$H-NMR (DMSO-$d_6$): δ 2.61 (3H, s), 3.38 (3H, s), 3.87 (3H, s), 7.47 (1H, ddd, J=2.5, 9.0, 9.0 Hz), 7.60 (1H, d, J=8.6 Hz), 7.83 (1H, dd, J=2.5, 9.9 Hz), 8.11 (1H, dd, J=4.7, 9.0 Hz), 8.22 (1H, dd, J=2.1, 8.6 Hz), 8.44 (1H, d, J=2.1 Hz), 8.63 (1H, s).

IR $ν_{max}$ (KBr): 3193, 3113, 3021, 3003, 2923, 1730, 1606, 1509, 1392, 1359, 1295, 1225, 1162, 1131, 988, 918 cm$^{-1}$.

Example 70

Synthesis of 2-[4-(5-fluoro-3-methylbenzo[b]thiophene-2-sulfonylamino)-3-methanesulfonylphenyl]thiazole-4-carboxylic Acid (Compound 70)

Into 45 mL of methanol was dissolved 954 mg of Compound 69, and 4.0 mL of 1 mol/L sodium hydroxide was added thereto. After 20 minutes of stirring under heating and refluxing, the solvent was removed by evaporation under reduced pressure, and the resulting residue was extracted with ether-water (1/1). To the aqueous layer was added 2 mol/L hydrochloric acid, and the precipitated crystals were washed with ether to obtain 746 mg of the title compound as colorless powder.

Melting point: 257–258° C.

$^1$H-NMR (DMSO-$d_6$): δ 2.59 (3H, s), 3.36 (3H, s), 7.45 (1H, ddd, J=2.3, 8.8, 8.8 Hz), 7.57 (1H, d, J=8.5 Hz), 7.81 (1H, dd, J=2.3, 9.9 Hz), 8.09 (1H, dd, J=5.0, 8.8 Hz), 8.18 (1H, dd, J=2.0, 8.5 Hz), 8.42 (1H, d, J=2.0 Hz), 8.51 (1H, s).

IR $ν_{max}$ (KBr): 3448, 3233, 3104, 3027, 2924, 1711, 1607, 1516, 1461, 1352, 1306, 1217, 1153, 1137 cm$^{-1}$.

Example 71

Synthesis of 5-fluoro-N-[2-methanesulfonyl-4-(2-methylthiazol-4-yl)phenyl]-3-methylbenzo[b]thiophene-2-sulfonamide (Compound 71)

Into 4.0 mL of chloroform was dissolved 200 mg of Compound 19, and 194 mg of benzyltrimethylammonium tribromide was added, followed by 1 hour of stirring at room temperature. The reaction was terminated by adding water to the reaction solution and then the solvent was once removed by evaporation. The residue was adjusted to pH 2 to 3 by adding 1 mol/L hydrochloric acid, followed by extraction with ethyl acetate. The organic layer was washed with saturated brine and then dried over anhydrous sodium sulfate. The solvent was removed by evaporation under reduced pressure and the resulting residue was washed with methanol to obtain 201 mg of N-(4-bromoacetyl-2-methanesulfonylphenyl)-5-fluoro-3-methylbenzo[b]thiophene-2-sulfonamide as a colorless solid. The thus obtained N-(4-bromoacetyl-2-methanesulfonylphenyl)-5-fluoro-3-methylbenzo[b]thiophene-2-sulfonamide (150 mg) was dissolved into a mixed solution of 1.5 mL of dioxane and 1.5 mL of ethanol, and 53 mg of sodium hydrogen carbonate and 26 mg of thioacetamide were successively added, followed by 2 hours of stirring under heating and refluxing. The reaction was terminated by adding water to the reaction solution and then the solvent was removed by evaporation under reduced pressure. The residue was adjusted to pH 2 to 3 by adding 1 mol/L hydrochloric acid, followed by extraction with ethyl acetate. The organic layer was washed with saturated brine and then dried over anhydrous sodium sulfate. The solvent was removed by evaporation under reduced pressure and the resulting residue was purified by silica gel column chromatography to obtain 61 mg of the title compound as light yellow powder.

Melting point: 217–220° C.

$^1$H-NMR (CDCl$_3$): δ 2.68 (3H, s), 2.75 (3H, s), 2.99 (3H, s) 7.27 (1H, ddd, J=2.4, 8.7, 9.0 Hz), 7.33 (1H, s), 7.45 (1H, dd, J=2.4, 9.3 Hz), 7.75 (1H, dd J=4.5, 9.0 Hz), 7.84 (1H, d, J=8.7 Hz), 8.06 (1H, dd, J=2.1, 8.7 Hz), 8.35 (1H, d, J=2.1 Hz), 9.55 (1H, s).

IR $ν_{max}$ (KBr): 3237, 1604, 1514, 1352, 1296, 1163, 899 cm$^{-1}$.

Example 72

Synthesis of 5-fluoro-N-[2-methanesulfonyl-4-((E)-2-methanesulfinyl-2-methylsulfanylvinyl)phenyl]-3-methylbenzo[b]thiophene-2-sulfonamide (Compound 72)

Under an argon atmosphere, 135 mg of the compound of Reference Example 3 was dissolved into 2 mL of THF, and 196 mg of methyl methylsulfinylmethyl sulfide and 862 μL of 40% methanol solution of Triton B were added successively, followed by 16 hours of stirring under heating and refluxing. After the reaction was terminated by adding 1 mol/L hydrochloric acid to the reaction solution, the mixture was diluted with ethyl acetate and the solution was washed with water and saturated brine, successively. After the solution was dried over anhydrous sodium sulfate, the solvent was removed by evaporation under reduced pressure and the resulting residue was purified by silica gel column chromatography (ethyl acetate/hexane=1/1) to obtain 105 mg of the title compound as colorless amorphous.

$^1$H-NMR (CDCl$_3$): δ 2.32 (3H, s), 2.70 (3H, s), 2.76 (3H, s), 3.04 (3H, s), 7.28 (1H, ddd, J=2.4, 9.0, 9.3 Hz), 7.48 (1H, dd, J=2.4, 9.3 Hz), 7.52 (1H, s), 7.78 (1H, dd J=4.8, 9.0 Hz), 7.83 (1H, d, J=8.7 Hz), 8.02 (1H, dd, J=2.1, 8.7 Hz), 8.46 (1H, d, J=2.1H z), 9.65 (1H, s).

IR $ν_{max}$ (KBr): 3446, 3225, 1604, 1492, 1303, 1163, 1133, 92 4 cm$^{-1}$.

The following show instrumental data in each Example.

TABLE 12

| Example | Melting point (° C.) | | H$^1$-NMR (δ) | IR (ν cm$^{-1}$, KBr) |
|---|---|---|---|---|
| 58 | 207–208 | CDCl$_3$ | 2.09(3H, s), 2.69 (3H, s), 3.00(3H, s), 3.98(3H, s), 7.46 (1H, dd, J = 1.9, 8.7 Hz), 7.73(1H, d, J = 8.7 Hz), 7.78 (1H, d, J = 1.9 Hz), 7.85(1H, d, J = 8.7 Hz), 8.07(1H, dd, J = 2.1, 8.7 Hz), 8.33(1H, d, J = 2.1 Hz), 9.64(1H, s). | 3423, 3021, 2931, 1658, 1482, 1351, 1296, 1281, 1163, 991, 929, 653 |
| 59 | 243–245 | CDCl$_3$ | 2.13(3H, s), 2.30 (3H, s), 2.68(3H, s), 3.01(3H, s), 6.83 (1H, d, J = 8.7 Hz), 7.27(1H, ddd, J = 2.4, 8.7, 9.0 Hz), | 3218, 1641, 1495, 1295, 1163, 913 |

TABLE 12-continued

| Example | Melting point (° C.) | H¹-NMR (δ) | | IR (ν cm⁻¹, KBr) |
|---|---|---|---|---|
| | | | 7.46(1H, dd, J = 2.4, 9.0 Hz), 7.75 (1H, dd, J = 4.5, 9.0 Hz), 7.87(1H, d, J = 8.7 Hz), 8.16 (1H, dd, J = 2.1, 8.7 Hz), 8.42(1H, d, J = 2.1 Hz), 9.66 (1H, s). | |
| 60 | Amorphous | DMSO-d₆ | 2.38(3H, s), 2.59 (3H, s), 3.34(3H, s), 7.04(1H, s), 7.48 (1H, ddd, J = 2.5, 8.9, 9.2 Hz), 7.60(1H, d, J = 8.6 Hz), 7.84(1H, dd, J = 2.5, 9.9 Hz), 8.12(1H, dd, J = 5.0, 8.9 Hz), 8.18 (1H, dd, J = 2.1, 8.6 Hz), 8.36(1H, d, J = 2.1 Hz). | 3161, 3089, 3000, 2912, 1653, 1613, 1498, 1308, 1156, 908, 647 |
| 61 | 176–179 | CDCl₃ | 1.39(3H, t, J = 6.9 Hz), 2.09(3H, s), 2.68(3H, s), 2.99 (3H, s), 4.22(2H, q, J = 2.1 Hz), 7.27 (1H, ddd, J = 2.4, 8.7, 9.0 Hz), 7.46 (1H, dd, J = 2.4, 9.0 Hz), 7.75(1H, dd, J = 4.5, 9.0 Hz), 7.86(1H, d, J = 8.7 Hz), 8.08(1H, dd, J = 2.1, 8.7 Hz) 8.33(1H, d, J = 2.1 Hz), 9.66(1H, s). | 3220, 1660, 1481, 1297, 1161, 923 |
| 62 | Amorphous | CDCl₃ | 2.35(3H, s), 2.38 (3H, s), 2.68(3H, s), 3.01(3H, s), 7.27 (1H, ddd, J = 2.4, 8.6, 8.8 Hz), 7.46 (1H, dd, J = 2.4, 9.2 Hz), 7.75(1H, dd, J = 4.7, 8.8 Hz), 7.83(1H, d, J = 8.7 Hz), 8.01(1H, dd, J = 2.1, 8.7 Hz), 8.32(1H, d, J = 2.1 Hz), 9.61(1H, s). | 3228, 3060, 3023, 2923, 1606, 1507, 1442, 1355, 1304, 1163, 1136, 925, 652 |
| 66 | 242–244 | DMSO-d₆ | 2.44(3H, s), 3.21 (3H, s), 4.28(2H, s), 7.31(1H, ddd, J = 2.0, 9.0, 9.0 Hz), 7.46(1H, d, J = 8.6 Hz), 7.65(1H, dd, J = 2.0, 8.0 Hz), 7.89(1H, s), 7.95 (1H, dd, J = 4.8, 9.0 Hz), 7.98(1H, d, J = 8.6 Hz), 8.24 (1H, s). | 3221, 3132, 2927, 1615, 1520, 1484, 1355, 1341, 1304, 1100 |
| 67 | 197–199 | CDCl₃ | 2.69(3H, s), 3.03 (3H, s), 4.53(2H, s), 7.27(1H, ddd, J = 2.4, 8.6, 8.6 Hz), 7.47(1H, dd, J = 2.4, 9.2 Hz), 7.70 (1H, s), 7.75(1H, dd, J = 4.8, 8.6 Hz), 7.92(1H, d, J = 8.8 Hz), 8.20(1H, dd, J = 2.0, 8.8 Hz), 8.49(1H, d, J = 2.0 Hz), 9.72(1H, s). | 3228, 2927, 1613, 1560, 1516, 1484, 1440, 1398, 1373, 1357, 1304, 1250, 1194, 1162, 1099 |
| 68 | 206–208 | CDCl₃ | 2.22(3H, s), 2.69 (3H, s), 3.02(3H, s), 7.28(1H, ddd, J = 2.4, 9.0, 9.0 Hz), 7.42(1H, d, J = 2.0 Hz), 7.46(1H, dd, J = 2.4, 9.2 Hz), 7.75(1H, dd, J = 4.8, 9.0 Hz), 7.89 (1H, d, J = 8.6 Hz), 8.17(1H, dd, J = 2.0, 8.6 Hz), 8.47 (1H, d, J = 2.0 Hz), 9.70(1H, s). | 3231, 3131, 2925, 1614, 1519, 1486, 1439, 1355, 1332, 1302, 1275, 1161, 1138, 1099 |

Example 73

Synthesis of 5-fluoro-N-[2-methanesulfonyl-4-(oxazol-2-yl)phenyl]-3-methylbenzo[b]thiophene-2-sulfonamide (Compound 73)

Compound 24 (902 mg) was melted over an open fire. The resulting caramel-like substance was purified by silica gel column chromatography (chloroform) and then recrystallized (ethyl acetate-hexane) to obtain 306 mg of the title compound as light yellow crystals.

Melting point: 207–208° C.

¹H-NMR (CDCl₃): δ 2.69 (3H, s), 3.03 (3H, s), 7.23 (1H, s), 7.27 (1H, ddd, J=2.6, 8.8, 8.8 Hz), 7.46 (1H, dd, J=2.6, 9.2 Hz), 7.71 (1H, s), 7.76 (1H, d, J=4.8, 8.8 Hz), 7.91 (1H, d, J=8.7 Hz), 8.21 (1H, dd, J=2.1, 8.7 Hz), 8.50 (1H, d, J=2.1 Hz), 9.70 (1H, s).

IR ν$_{max}$ (KBr): 3237, 3140, 3020, 2925, 1615, 1519, 1481, 1354, 1303, 1163, 1139, 912, 650 cm⁻¹.

Example 74

Synthesis of methyl (4R)-2-[4-(5-fluoro-3-methylbenzo[b]thiophene-2-sulfonylamino)-3-methanesulfonylphenyl]thiazoline-4-carboxylate (Compound 74)

Into 1500 mL of dichloromethane was dissolved 31.04 g of methyl (2R)-2-[4-(5-fluoro-3-methylbenzo[b]thiophene-2-sulfonylamino)-3-methanesulfonylphenylcarboxyamido]-3-tritylthiopropionate. After the solution was cooled to 0° C., 19.8 mL of hexamethylphosphoramide was added and 435 mL of dichloromethane solution of 12.9 mL of titanium tetrachloride was added dropwise (Tetrahedron Letters, 42, 4171 (2001)). After 21 hours of stirring at room temperature, the reaction was terminated by adding water. The solvent was removed by evaporation under reduced pressure and the resulting residue was re-dissolved into ethyl acetate. The solution was washed with water and saturated brine, successively. After drying over anhydrous sodium sulfate, the solvent was removed by evaporation under reduced pressure and the resulting residue was purified by silica gel column chromatography (chloroform) and then recrystallized from chloroform-hexane to obtain 11.09 g of the title compound as colorless powder.

Melting point: 170–171° C.

¹H-NMR (CDCl₃) δ 2.68 (3H, s), 3.03 (3H, s), 3.66 (1H, dd, J=9.1, 11.5 Hz), 3.73 (1H, dd, J=9.1, 11.5 Hz), 3.82 (3H, s), 5.25 (1H, t, J=9.1 Hz), 7.28 (1H, ddd, J=2.5, 8.7, 8.9 Hz), 7.46 (1H, dd, J=2.5, 9.2 Hz), 7.76 (1H, dd, J=4.7, 8.9 Hz), 7.85 (1H, d, J=8.6 Hz), 8.01 (1H, dd, J=2.0, 8.6 Hz), 8.31 (1H, d, J=2.0 Hz), 9.76 (1H, s).

IR $v_{max}$ (KBr): 3186, 3029, 3000, 2954, 2920, 1744, 1606, 1498, 1357, 1293, 1225, 1163, 1131, 989, 927 $cm^{-1}$.

Example 75

5-Fluoro-N-(4-hydroxymethyl-2-methanesulfonylphenyl)-3methylbenzo[b]thiophene-2-sulfonamide Into 120 mL of toluene was dissolved 2.08 g of Compound 17. After cooling to −30° C., 22.5 mL of 1.01 mol/L toluene solution of diisobutylaluminum hydride was added thereto. After 5 hours of stirring at the same temperature, water was added to the reaction solution to terminate the reaction and then the mixture was diluted with ethyl acetate, followed by addition of saturated aqueous potassium sodium tartrate solution and 30 minutes of stirring at room temperature. The mixture was extracted with ethyl acetate and the organic layer was washed with saturated brine and then dried over anhydrous sodium sulfate. The solvent was removed by evaporation under reduced pressure and the resulting residue was purified by silica gel column chromatography (ethyl acetate/hexane=1/1) to obtain 1.38 g of the title compound as colorless powder.

Melting point: 120–121° C.

$^1$H-NMR (CDCl$_3$): δ 2.68 (3H, s), 2.96 (3H, s), 4.68 (2H, s), 7.26(1H, ddd, J=2.4, 8.7, 9.0 Hz), 7.46 (1H, dd, J=2.4, 9.0 Hz), 7.57 (1H, dd, J=1.8, 8.4 Hz), 7.75 (1H, dd, J=4.5, 8.7 Hz), 7.77 (1H, d, J=8.4 Hz), 7.86 (1H, d, J=1.8 Hz), 9.48 (1H, s).

IR $v_{max}$ (KBr): 3504, 3221, 1608, 1497, 1347, 1296, 1150, 926 $cm^{-1}$.

Test Example 1

Measurement of Inhibitory Activity of Simian Chymase or Human Chymase

Simian chymase used was obtained from the heart of rhesus monkey through purification in accordance with a human heart chymase purification method (J. Biol. Chem., 265, 22348 (1990)), and human chymase used was obtained from silkworms infected with baculovirus integrated with a gene encoding human chymase (FEBS. Let., 412, 86 (1997)).

Chymase activity was determined with reference to the method known in a literature (Miyazaki et al., Kekkan, Vol. 20, p. 207 (1997)). That is, the activity was measured by reacting free His-Leu formed together with Ang II with o-phthalaldehyde (hereinafter, abbreviated as OPT) to prepare a fluorescent derivative and determining the amount quantitatively by means of a fluorophotometer.

First, 3.6 μmol of each test compound was weighed in a test tube and was dissolved into 3 mL of DMSO. The DMSO solution was diluted 1000-fold with 20 mmol/L Tris-hydrochloric acid buffer solution (pH 8.0) containing 0.01% Triton X-100 and 0.5 mol/L potassium chloride to prepare $1.2 \times 10^{-6}$ mol/L solution, which was successively diluted with the buffer solution to prepare test sample solutions having concentrations of $1.2 \times 10^{-6}$ mol/L to $1.2 \times 10^{-9}$ mol/L. To 500 μL of the test sample solution of each concentration or buffer solution was added 50 μL of an enzyme solution, followed by 10 minutes of pre-incubation at 37° C. Then, 50 μL of 0.1 mmol/L Ang I solution was added to initiate a reaction. Human angiotensin I (manufactured by SIGMA) was employed as Ang I. The enzyme solution to be used for the reaction was adjusted so as to hydrolyze about 60% of substrate under the conditions, and the reaction wherein a buffer solution containing no enzyme was carried out as a blind test. After 120 minutes of incubation at 37° C., the reaction was terminated by adding 900 μL of 15% of trichloroacetic acid. Thereafter, the reaction mixture was centrifuged at 4° C. at 3,000 rpm for 10 minutes and 2 mL of 2 mol/L sodium hydroxide and 1 mL of methanol were added to 1 mL of the resulting supernatant. Thereto was added 100 μL of methanol solution containing 1.2 mg of N-acetyl-L-cysteine and 1 mg of OPT per 1 mL, whereby a derivatization reaction was initiated. After the reaction mixture was left on standing for exactly 1 hour, fluorescence intensity at fluorescence wavelength of 502 nm under excitation wavelength of 304 nm was measured. The measurement was repeated twice for each sample and blind test. The fluorescence intensity obtained by subtracting the average value at blind test from the average value thereof was determined as chymase activity.

In this regard, an enzymatic reaction using a buffer solution instead of the test sample solution was carried out as a control, and inhibitory ratio of chymase activity was determined as percentage by dividing the difference of subtraction of the activity at the addition of the test compound from the chymase activity at the control by the chymase activity at the control. Based on each inhibitory ratio, the concentration at which 50% of the activity was inhibited (hereinafter, referred to as $IC_{50}$ value) was calculated. Table 13 shows $IC_{50}$ values of representative compounds.

TABLE 13

| Compound | Simian chymase $IC_{50}$ value (nmol/L) | Human cymase $IC_{50}$ value (nmol/L) |
|---|---|---|
| Compound 1 | 50 | 203 |
| Compound 2 | 42 | |
| Compound 3 | 178 | |
| Compound 4 | 111 | |
| Compound 5 | 150 | |
| Compound 7 | 185 | |
| Compound 8 | 159 | |
| Compound 11 | 100 | 271 |
| Compound 13 | 271 | |
| Compound 14 | 278 | |
| Compound 17 | 9 | 56 |
| Compound 19 | 20 | 82 |
| Compound 20 | 39 | 305 |
| Compound 24 | 2 | 37 |
| Compound 25 | 75 | |
| Compound 26 | 10 | 150 |
| Compound 48 | 6 | 45 |
| Compound 52 | 157 | |
| Compound 56 | | 102 |
| Compound 63 | | 20 |
| Compound 66 | | 39 |
| Compound 68 | | 101 |
| Compound 70 | 0.4 | 7 |
| Compound 72 | | 20 |
| Compound 73 | | 55 |

Test Example 2

Measurement of Cathepsin G Inhibitory Activity and Chymotrypsin Inhibitory Activity Each activity of cathepsin G or chymotrypsin was measured by determining the amount of free p-nitroaniline quantitatively using a synthetic substrate that is colorless and yields colored product upon hydrolysis, by means of a spectrophotometer. Chymotrypsin Type I-S derived from bovine pancreas was purchased from SIGMA. As cathepsin G, the product of Elastin Products Company, Inc. derived from human purulent sputum was used. Suc-Ala-Ala-Pro-Phe-pNA (manufactured by SIGMA) was used as the synthetic substrate. An inhibitory effect of a compound on each enzyme was determined by the following method.

Each test compound (5 μmol) was weighed in a test tube and dissolved into 2 mL of DMSO. The DMSO solution was diluted 100-fold with 20 mmol/L Tris-hydrochloric acid buffer solution (pH 7.5) containing 0.01% Triton X-100 and 0.5 mol/L potassium chloride to prepare $2.5 \times 10^5$ mol/L solution, which was successively diluted to prepare test sample solutions having concentrations of $2.5 \times 10^{-5}$ mol/L to $2.5 \times 10^{-9}$ mol/L. To 200 μL of each test sample solution or buffer solution was added 100 μL of an enzyme solution of 40 μg/mL chymotrypsin or 8 units/mL cathepsin G, followed by 10 minutes of pre-incubation at 37° C. Then, 200 μL of 1 mmol/L substrate solution was added to initiate en enzymatic reaction under a temperature of 37° C. A reaction wherein a buffer solution containing no enzyme was carried out as a blind test, and incubation time was 30 minutes and 60 minutes for chymotrypsin and cathepsin G, respectively. After the incubation, the reaction was terminated by adding 300 μL of 50% acetic acid, and absorbance at 405 nm was measured. The measurement was repeated twice for each sample and blind test. The absorbance obtained by subtracting the average value at blind test from the average value of each sample was determined as activity of each enzyme.

In this regard, an enzymatic reaction using a buffer solution instead of the test sample solution was carried out as a control, and inhibitory ratio of each enzyme activity was determined as percentage by dividing the difference from the subtraction of the activity at the addition of the test compound from the enzyme activity at the control by the enzyme activity at the control. Based on each inhibitory ratio, $IC_{50}$ value was calculated.

Table 14 shows $IC_{50}$ values of inhibitory activities of the representative Compounds against Cathepsin G and Chymotrypsin.

TABLE 14

Inhibitory specificity of active compounds

| Compound | IC$_{50}$ value (nmol/L) | |
| --- | --- | --- |
| | Chymotrypsin | Cathepsin G |
| Chymostatin | 9.67 | 5.99 |
| Compound 1 | >10000 | >10000 |
| Compound 4 | >10000 | >10000 |
| Compound 5 | >1000 | >1000 |
| Compound 7 | >1000 | >1000 |
| Compound 8 | >10000 | >10000 |
| Compound 14 | >10000 | >10000 |
| Compound 17 | >10000 | >10000 |
| Compound 24 | >10000 | >10000 |
| Compound 26 | >10000 | >10000 |
| Compound 48 | >10000 | >10000 |
| Compound 70 | >10000 | >10000 |

Test Example 3

Stability in Rat Plasma

Stability of the compounds of the invention in rat plasma was investigated.

Male SD rats (7-week-old) were anesthetized with ether under over-night fasting conditions and, after an abdominal part was incised, blood was collected from aorta abdominalis using a heparinized disposable plastic syringe. The blood was centrifuged under cooling to collect a supernatant plasma. The collected plasma was stored under freezing at −30° C. and was melted before use. After a test compound was dissolved in DMSO, the solution was added to 200 μL of the plasma so as to be 10 μg/mL, followed by incubation at 37° C. After 60 minutes, the mixture was acidified by adding 200 μL of 0.1 mol/L hydrochloric acid, and then extracted twice with 2 mL of ethyl acetate. The resulting organic layer was evaporated to dryness under a nitrogen gas flow and the residue was dissolved into 200 μL of acetonitrile to prepare a sample solution. On the other hand, the test compound was dissolved into 1% acetonitrile solution of DMSO so as to be 10 μg/mL as a control solution. The sample solution and control solution was investigated by high performance liquid chromatography (hereinafter, abbreviated as HPLC). Residual ratio (%) was determined as percentage by dividing the peak area of the sample solution by the peak area of the control solution.

HPLC Conditions:

Column: Waters Nova Pack $C_{18}$ (inner diameter: 3.9 mm, length: 150 mm)

Mobile phase A: acetonitrile/water=10/90

Mobile phase B: acetonitrile/methanol=50/50

Eluent: Mobile phase A-mobile phase B (100/0 to 0/100, linear gradient, 50 minutes)

Flow rate: 1.0 mL/minute

Amount of injection: 50 μL

Table 15 shows residual ratios of representative compounds in rat plasma.

TABLE 15

| Compound | Residual ratio in rat plasma (%) |
| --- | --- |
| Compound 1 | 93.9 |
| Compound 4 | 93.5 |
| Compound 5 | 85.2 |
| Compound 7 | 96.4 |
| Compound 8 | 92.0 |
| Compound 14 | 79.2 |
| Compound 19 | 96.2 |
| Compound 24 | 100 |
| Compound 26 | 100 |

Test Example 4

Test in Rat Monocrotaline-Induced Pulmonary Hypertension Model

Into 1.2 mL of 1 mol/L hydrochloric acid was dissolved 200 mg of monocrotaline, followed by addition of 5 mL of distilled water. The solution was neutralized with 0.5 mol/L sodium hydroxide, and further diluted with distilled water so as to be 10 mL (20 mg/mL). Moreover, a solution containing the solvent alone without monocrotaline was prepared as Solvent A. A test compound was suspended into olive oil (25 mg/mL). Furthermore, a solution containing no test compound but the solvent alone was prepared as Solvent B.

Monocrotaline (60 mg/kg-body weight) was administrated subcutaneously at the posterior region of neck of five 5-week-old SD male rats. From 3 days before monocrotaline administration to 20 days after the administration, a test compound was administered intraperitoneally twice a day at a dose of 50 mg/kg-body weight. On the next day of the final administration of the test compound, the rats were fixed supinely under anesthetization with intraperitoneal administration of sodium pentobarbital. And then blood pressure was measured with cannula inserted from left carotid artery and systolic pressure at right ventricle was measured with cannula inserted from right carotid artery and introduced into right ventricle, via a pressure transducer by means of a pressure-strain gauge. After slaughter of the animals, the heart was removed and weight of right ventricle, weight of left ventricle and septum, and diameter and medial thickness of pulmonary artery having a diameter within a range of 50 to 150 μm were measured. Moreover, from these measured values, a weight ratio of right ventricle/(left ventricle+septum) and medial thickening ratio {(medial thickness/outer diameter of the blood vessel)×100} were determined. In this regard, a group wherein the rats to which monocrotaline was administered was treated with Solvent B alone in an amount of 2 mL/kg-body weight in the same administration schedule as above was named "Solvent-administered group". In addition, a group wherein the rats to which Solvent A was administered in an amount of 3 mL/kg-body weight was treated with Solvent B in an amount of 2 mL/kg-body weight was named "Monocrotaline-untreated group". The results are shown in Table 16.

TABLE 16

| | | Monocotaline-treated group | |
|---|---|---|---|
| | Monocrotaline-untreated group | Solvent-administered group | Test compound group (Compound 17) |
| Number of rats | 5 | 4 to 5 | 3 to 4 |
| Average blood pressure (mmHg) | 105 ± 11 | 85 ± 6 | 111 ± 19 |
| Systolic pressure at right ventricle | 29 ± 2 | 63 ± 15 | 57 ± 11 |
| Weight of right ventricle (mg) | 154 ± 7 | 246 ± 30 | 233 ± 24 |
| Weight ratio of right ventricle/(left ventricle + septum) | 0.24 ± 0.00 | 0.44 ± 0.05 | 0.39 ± 0.04 |
| Medial thickening ratio | 7.16 ± 0.58 | 14.28 ± 2.13 | 10.55 ± 1.80 |

In the group to which a test compound (Compound 17) was administered, thickening of medial muscular layer (increase of medial thickening ratio) appearing as a result of progress of pulmonary hypertension was suppressed. Since the test compound exhibited a tendency of suppressing the thickening of medial muscular layer and of suppressing the increase of weight of right ventricle without lowering systemic blood pressure in monocrotaline-induced pulmonary hypertension model, it was confirmed that the compound of the invention was effective for preventing and treating pulmonary hypertension.

Test Example 5

Investigation in Hamster Adhesion Model

Five-week-old female hamster (10 hamsters per each group) was anesthetized by administering intraperitoneally pentobarbital sodium (50 mg/kg) and, after midline incision at abdominal region, the uterus was rubbed with a cotton swab. Thereafter, 1 mL of saline solution of a test compound (Compound 24: $10^{-4}$ mol/L) was added dropwise intraperitoneally, and then the incised part was sutured. On the other hand, as a control, saline alone was added dropwise, followed by a similar treatment.

After 4 weeks from the operation, the animals were slaughtered, the abdominal part was exposed and adhesion was investigated. The adhesion was judged using the following 5-grade scoring system and the data were analyzed according to Mann-Whitney U test.

Adhesion Score
  0: No adhesion
  1: Very weak adhesion (film-like adhesion easily releasable)
  2: Limited adhesion (strong adhesion difficult to release at only one point)
  3: Wide-range adhesion (strong adhesion difficult to release at several points)
  4: Very strong adhesion (very strong adhesion impossible to release)

As a result, average score of the control group was 2.0, while average score of the group to which a test compound (Compound 24) was administered was 0.9. Thus, postoperative adhesion was significantly suppressed ($p<0.05$).

Test Example 6

Investigation in Rat Cecum-scraped Adhesion Model

Six-week-old SD rats were subjected to midline incision at lower abdominal region under pentobarbital anesthetization (70 mg/kg, intramuscular injection), and the cecum was taken out of the incised part. Two parts of serous membrane of the cecum (about 2 $cm^2$ each) were rubbed with a cotton swab a hundred times until petechial hemorrhage occurs, followed by dropwise addition of 100 μL of ethanol. The cecum was again set in abdominal cavity, and then, 2 mL of a phosphate buffered saline (hereinafter, abbreviated as PBS, pH 7.4) solution of a test compound (Compound 24 or 70) was added dropwise intraperitoneally, and then the incised part was sutured. The concentration of each test compound solution was $10^{-5}$ mol/L in a control group, PBS alone was added dropwise, followed by a similar treatment. Each group had 11 or 12 rats. After 1 week from the operation, the animals were slaughtered, the abdominal part was re-incised and an adhesion state of the cecum was evaluated according to adhesion scores using the adhesion intensity and adhesion area as indexes. The score values were determined according to the following 5-grade scores. In this connection, adhered region (%) was determined as percentage of total area of the adhered parts relative to the area of the rubbed regions.

Adhesion Score
  0: No adhesion
  1: Easily releasable adhesion limited to only a part (less than 25% of adhered region)
  2: Easily releasable adhesion over a wide range (25% or more of adhered region) or limited adhesion to only a part (less than 25% of adhered region) difficult to release
  3: Wide-range adhesion (25% or more of adhered region) difficult to release
  4: Adhesion impossible to release or adhesion accompanied by serous membrane injury at release As a result, with regard to adhesion score distribution, total percentage of scores 3 and 4 showing severe adhesions was 63.6% in the control group, while the percentage decreased to 41.7% and 33.3% in the administered groups of administering $10^{-5}$ mol/L solution of Compound 24 and Compound 7, respectively. Thus, adhesion was suppressed by administering the compounds.

Test Example 7

Investigation in Canine Eye Postoperative Adhesion Model

A beagle dog was anesthetized and each conjunctiva of both eyes thereof was peeled in a size of 10 mm×5 mm under a stereomicroscope. At that time, Tenon was left at conjunctival side and was not left at scleral side. After a sponge immersed in a saline solution of a test compound (Compound 70) was placed at the incised part for 3 minutes, the incised part was put in one stitch with 10-0 nylon thread. The concentration of the test compound solution was $10^{-4}$ mol/L and a saline was used in a control group (6 dogs per each group).

After 7 days from the operation, the animals were slaughtered, the eyeballs were taken out and adhesion was investigated. After the thread used at the stitching in the model preparation was cut, evaluation was carried out by pulling the conjunctiva part with tweezers and scoring the adhesion state. The score values were determined according to the following 5-grade scores, and Mann-Whitney U test was used for analyzing the data.

Adhesion Score

0: No adhesion

1: Very weak adhesion (film-like adhesion easily releasable)

2: Limited adhesion (strong adhesion difficult to release at only one point)

3: Wide-range adhesion (strong adhesion difficult to release at several points)

4: Very strong adhesion (very strong adhesion impossible to release)

As a result, average score of the control group was 3.67, while average score of the test compound (Compound 70) group was 2.67. Thus, postoperative adhesion was significantly suppressed ($p<0.05$).

Formulation Example 1

Manufacture of Tablets

Tablets having 200 mg weight and containing 5 mg of Compound 24 per tablet were manufactured by mixing 5 g of Compound 24, 125 g of lactose, 40 g of corn starch and 20 g of crystalline cellulose, adding 10% ethanol solution of 6 g of hydroxypropyl cellulose, kneading and granulating the mixture, preparing granules by extrusion through a screen having a mesh size of 8 mm, adding 4 g of magnesium stearate after drying the granules, and subjecting the mixture to compression molding.

Formulation Example 2

Manufacture of Injections or Liquids

After 50 mg of Compound 24 and 900 mg of sodium chloride were dissolved in 90 mL of water for injection, the solution was adjusted to pH 7 with 0.1 mmol/L sodium hydroxide and total amount was made 100 mL using water for injection. Then, the solution was aseptically filtered, and 2 mL of the filtrate was charged into each glass ampoule to manufacture injections or liquids containing 1 mg of Compound 24 per ampoule.

Formulation Example 3

Manufacture of Suppositories

Witepsol H-15 was heated to melt and Compound 24 was added so as to be 10 mg/mL, followed by homogeneous mixing. Two mL of this mixture was injected into each plastic container for suppository and cooled to manufacture suppositories containing 20 mg of Compound 24 per suppository.

Formulation Example 4

Manufacture of Eye-Drops

Into 80 mL of purified water were dissolved 50 mg of Compound 24, 0.1 g of sodium dihydrogen phosphate dihydrate, 0.9 g of sodium chloride and 5 mg of benzalkonium chloride, and 0.1 mol/L aqueous sodium hydroxide solution was added to adjust the solution to pH 7, followed by adding purified water to make total volume 100 mL. After the solution was aseptically filtered, 5 ml of the filtrate was charged into each polypropylene container for eye-drops to manufacture 0.05% eye-drops of Compound 24.

Formulation Example 5

Manufacture of Aerosol

After 100 mg of Compound 17 was suspended into 10 g of ethanol, 3 g of the liquid was charged into a pressure-resistant aluminum container, and then the valve part was firmly fixed. Into the container was charged 4.2 g of 1,1,1,2-tetrafluoroethane to form an aerosol.

Industrial Applicability

The N-substituted benzothiophenesulfonamide derivatives or pharmaceutically acceptable salts thereof of the invention have a selective inhibitory action on chymase and are useful as agents for preventing or treating cardiac and circulatory diseases, especially cardiac infarction, restenosis after PTCA and intimal thickening after bypass grafting, pulmonary hypertension caused by abnormal increase of production of angiotensin II or endothelin I based on chymase activity, or by activation of mast cell, and are useful as agents for preventing adhesion after surgery.

What is claimed is:

1. An N-substituted benzothiophenesulfonamide derivative represented by formula (I):

$$\text{(I)}$$

wherein
- $R^1$ represents a hydrogen atom, a halogen atom or a lower alkyl group;
- $R^2$ represents a lower alkyl group;
- $R^3$ and $R^4$ each may be the same or different and represents a hydrogen atom, a lower alkoxycarbonyl group, a lower alkylsulfonyl group, a benzoyl group, an acyl group having 1 to 4 carbon atoms, a lower alkoxy group, a lower alkoxycarbonylmethylthioacetyl group, a nitro group, —CONHR⁶ in which R⁶ represents a hydrogen atom, a lower alkoxycarbonylmethyl group, a carboxymethyl group or —CH(CH₂OH)COOR⁷ which R⁷ represents a hydrogen atom or a lower alkyl group, a group represented by formula:

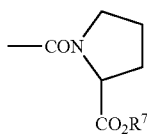

in which R⁷ has the same meaning as above, a group represented by formula:

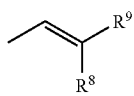

in which R⁸ and R⁹ each may be the same or different and represents a hydrogen atom, a lower alkyl group, a lower alkylsulfanyl group, a lower alkylsulfinyl group, a lower alkylsulfonyl group or a lower alkoxycarbonyl group, a hydroxy lower alkyl group, a cyano group or a monocyclic heterocyclic group represented by formulae:

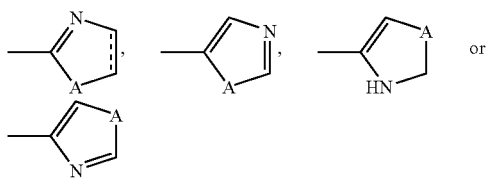

in which A represents an oxygen atom, a sulfur atom or NH and the dotted part represents a single bond or a double bond provided that the hydrogen atom on the ring may be replaced by a lower alkyl group which may be substituted by a halogen atom, a lower alkoxy group, a hydroxy lower alkyl group, a lower alkoxycarbonyl group or a carboxyl group, provided that at least one of R³ or R⁴ is

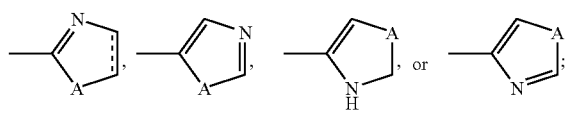

and

R⁵ represents a hydrogen atom, a lower alkoxy group or a lower alkyl group, except the compounds represented by formulae:

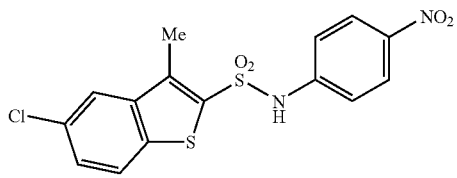

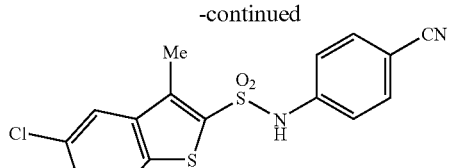

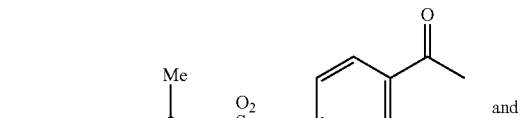

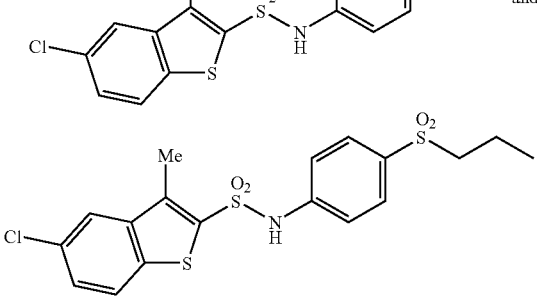

or a pharmaceutically acceptable salt thereof.

2. The N-substituted benzothiophenesulfonamide derivative according to claim 1, wherein said derivative or a pharmaceutically acceptable salt thereof is selected from the group consisting of 2-]4-(5-chloro-3-methylbenzo[b]thiophene-2-sulfonylamino)-3-methanesulfonylphenyl]oxazole-4-carboxylic acid, 2-[4-(5-fluoro-3-methylbenzo[b]thiophene-2-sulfonylamino)-3-methanesulfonylphenyl]oxazole-4-carboxylic acid, disodium 2-[4-(5-chloro-3-methylbenzo[b]thiophene-2-sulfonylamino)-3-methanesulfonylphenyl]oxazole-4-carboxylate, disodium 2-[4-(5-fluoro-3-methylbenzo[b]thiophene-2-sulfonylamino)-3-methanesulfonylphenyl]oxazole-4-carboxylate, 2-]4-(5-fluoro-3-methylbenzo[b]thiophene-2-sulfonylamino)-3-methanesulfonylphenyl]thiazole-4-carboxylic acid, 5-fluoro-N-[4-(4-hydroxymethylthiazol-2-yl)-2-methanesulfonylphenyl]-3-methylbenzo[b]thiophene-2-sulfonamide, 5-fluoro-N-[2-methanesulfonyl-4-(5-methoxy-4-methyloxazol-2-yl)phenyl]-3-methylbenzo[b]thiophene-2-sulfonamide, and 5-fluoro-N-[2-methanesulfonyl-4-(5-methyloxazol-2-yl)phenyl]-3-methylbenzo[b]thiophene-2-sulfonamide.

3. A pharmaceutical composition comprising an N-substituted benzothiophenesulfonamide derivative represented by formula (I):

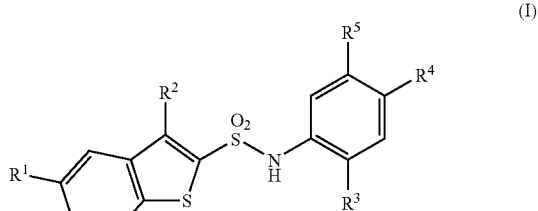

wherein R¹ represents a hydrogen atom, a halogen atom or a lower alkyl group;

$R^2$ represents a lower alkyl group;

$R^3$ and $R^4$ each may be the same or different and represents a hydrogen atom, a lower alkoxycarbonyl group, a lower alkylsulfonyl group, a benzoyl group, an acyl group having 1 to 4 carbon atoms, a lower alkoxy group, a lower alkoxycarbonylmethylthioacetyl group, a nitro group, —$CONHR^6$ in which $R^6$ represents a hydrogen atom, a lower alkoxycarbonylmethyl group, a carboxymethyl group or —$CH(CH_2OH)COOR^7$ in which $R^7$ represents a hydrogen atom or a lower alkyl group, a group represented by formula:

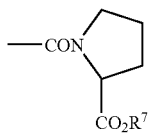

in which $R^7$ has the same meaning as above, a group represented by formula:

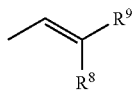

in which $R^8$ and $R^9$ each may be the same or different and represents a hydrogen atom, a lower alkyl group, a lower alkylsulfanyl group, a lower alkylsulfinyl group, a lower alkylsulfonyl group or a lower alkoxycarbonyl group, a hydroxy lower alkyl group, a cyano group or a monocyclic heterocyclic group represented by formulae:

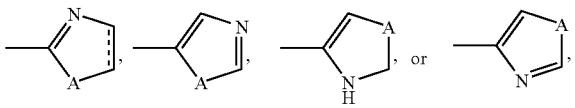

in which A represents an oxygen atom, a sulfur atom or NH and the dotted part represents a single bond or a double bond provided that the hydrogen atom on the ring may be replaced by a lower alkyl group which may be substituted by a halogen atom, a lower alkoxy group, a hydroxy lower alkyl group, a lower alkoxycarbonyl group or a carboxyl group, provided that at least one of $R^3$ or $R^4$ is

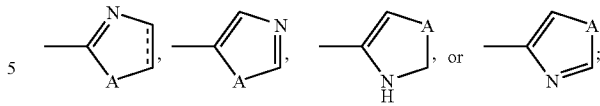

and $R^5$ represents a hydrogen atom, a lower alkoxy group or a lower alkyl group, or a pharmaceutically acceptable salt thereof.

4. A chymase inhibitor comprising the pharmaceutical composition of claim 3.

5. An agent for treating hypertension, hypercardia, cardiac failure, cardiac infarction, arteriosclerosis, diabetic or non-diabetic renal disease, diabetic retinopathy, ischemic re-perfusion disorder, restenosis after percutaneous transluminal coronary angioplasty, intimal thickening after bypass grafting, chronic rheumatism, keloid, psoriasis, allergy, inflammation, asthma, atopic dermatitis, solid tumors, or pulmonary hypertension, wherein the agent comprises the pharmaceutical composition of claim 3.

6. An agent for suppressing tissue adhesion comprising the pharmaceutical composition of claim 3.

7. A method of treating a disorder selected from hypertension, hypercardia, cardiac failure, cardiac infarction, arteriosclerosis, diabetic or non-diabetic renal disease, diabetic retinopathy, isehemic re-perfusion disorder, restenosis after percutaneous transluminal coronary angioplasty, intimal thickening after bypass grafting, chronic rheumatism, keloid, psoriasis, allergy, inflammation, asthma, atopic dermatitis, solid tumors, and pulmonary hypertension in a patient in need thereof comprising administering to the patient an effective amount of the pharmaceutical composition of claim 3.

8. The method of claim 7, wherein the disorder is hypercardia.

9. The method of claim 7, wherein the disorder is cardiac failure.

10. The method of claim 7, wherein the disorder is cardiac infarction.

11. The method of claim 7, wherein the disorder is diabetic renal disease or non-diabetic renal disease.

12. The method of claim 7, wherein the disorder is isehemic re-perfusion disorder.

13. The method of claim 7, wherein the disorder is pulmonary hypertension.

14. A method of suppressing tissue adhesion following surgery in a patient in need thereof comprising administering to the patient an effective amount of the pharmaceutical composition of claim 3.

* * * * *

UNITED STATES PATENT AND TRADEMARK OFFICE
CERTIFICATE OF CORRECTION

PATENT NO.        : 7,071,220 B2                                    Page 1 of 1
APPLICATION NO.   : 10/388378
DATED             : July 4, 2006
INVENTOR(S)       : Shoji Satoh et al.

It is certified that error appears in the above-identified patent and that said Letters Patent is hereby corrected as shown below:

On the title page item (75), delete the following six Inventors:

"Akira Tatsui, Fukushima (JP)"

"Takeshi Hasegawa, Fukushima (JP)"

"Hideki Yamada, Saitama (JP)"

"Shin-ichi Kazayama, Saitama (JP)"

"Takahiro Morita, Saitama (JP)"

"Atsuo Takahashi, Saitama (JP)"

Signed and Sealed this

Sixth Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,071,220 B2  Page 1 of 1
APPLICATION NO. : 10/388378
DATED : July 4, 2006
INVENTOR(S) : Shoji Satoh et al.

It is certified that error appears in the above-identified patent and that said Letters Patent is hereby corrected as shown below:

Title page item [75]
Please delete the following six Inventors:

"Akira Tatsui, Fukushima (JP)"

"Takeshi Hasegawa, Fukushima (JP)"

"Hideki Yamada, Saitama (JP)"

"Shin-ichi Kazayama, Saitama (JP)"

"Takahiro Morita, Saitama (JP)"

"Atsuo Takahashi, Saitama (JP)"

Signed and Sealed this

Twelfth Day of June, 2007

JON W. DUDAS
*Director of the United States Patent and Trademark Office*